US008586081B2

(12) United States Patent
Singh et al.

(10) Patent No.: US 8,586,081 B2
(45) Date of Patent: Nov. 19, 2013

(54) DETOXIFIED RECOMBINANT BOTULINUM NEUROTOXIN

(75) Inventors: Bal Ram Singh, Dartmouth, MA (US); Weiping Yang, Dartmouth, MA (US)

(73) Assignee: University of Massachusetts, Boston, MA (US)

( * ) Notice: Subject to any disclaimer, the term of this patent is extended or adjusted under 35 U.S.C. 154(b) by 278 days.

(21) Appl. No.: 12/233,799

(22) Filed: Sep. 19, 2008

(65) Prior Publication Data

US 2009/0155348 A1 Jun. 18, 2009

Related U.S. Application Data

(60) Provisional application No. 60/994,603, filed on Sep. 20, 2007.

(51) Int. Cl.
*A61K 39/08* (2006.01)
(52) U.S. Cl.
USPC ......... 424/450; 424/239.1; 530/300; 530/350
(58) Field of Classification Search
None
See application file for complete search history.

(56) References Cited

U.S. PATENT DOCUMENTS

| | | | |
|---|---|---|---|
| 4,109,496 | A | 8/1978 | Allemann et al. |
| 4,868,103 | A | 9/1989 | Stavrianopoulos et al. |
| 5,177,016 | A | 1/1993 | Balsari et al. |
| 5,223,409 | A | 6/1993 | Ladner et al. |
| 5,283,317 | A | 2/1994 | Saifer et al. |
| 5,364,634 | A | 11/1994 | Lew |
| 5,631,169 | A | 5/1997 | Lakowicz et al. |
| 6,203,794 | B1 * | 3/2001 | Dolly et al. ................ 424/184.1 |
| 6,231,855 | B1 | 5/2001 | Ghione et al. |
| 6,967,088 | B1 * | 11/2005 | Williams et al. ............ 435/69.1 |

(Continued)

FOREIGN PATENT DOCUMENTS

| | | | |
|---|---|---|---|
| EP | 1 334 721 A1 | * | 8/2003 |
| EP | 1334729 | * | 8/2003 |

(Continued)

OTHER PUBLICATIONS

Smith (Vaccine, vol. 27, Supplement 4, pp. D33-D39).*

(Continued)

*Primary Examiner* — Albert Navarro
*Assistant Examiner* — Ginny Portner
(74) *Attorney, Agent, or Firm* — Medlen & Carroll, LLP

(57) ABSTRACT

The present invention relates to the isolation of polypeptides derived from the *Clostridium botulinum* neurotoxin and the use thereof as immunogens for the production of vaccines and antitoxins, as well as research and drug development applications. *Clostridium botulinum* is responsible for food bone botulism, a severe and often deadly disease. Botulinum neurotoxin binds to neural cells and are translocated into the cytosol. The toxin then prevents neurotransmitter release by cleaving a SNARE protein. A double mutant E224A/E262 full length botulinum neurotoxin Type A holo form was successfully cloned and purified, which lacks the endopeptidase activity involved in the toxic action of the BoNT, and thus leading to its detoxification (DR BoNT/A). This new molecule can be used as an antidote against botulism, and also as a vaccine candidate for botulism. Due to the poor availability and extreme toxicity of native holo-toxin, a nontoxic form of the holo-toxin is highly desired for research and vaccine development. The full length DR BoNT/A protein has been expressed in *E. coli* as a soluble form.

11 Claims, 11 Drawing Sheets
(1 of 11 Drawing Sheet(s) Filed in Color)

(56) References Cited

U.S. PATENT DOCUMENTS

| | | | | |
|---|---|---|---|---|
| 7,081,529 | B2* | 7/2006 | Smith et al. | 536/23.7 |
| 7,341,843 | B2* | 3/2008 | Atassi | 435/7.32 |
| 7,628,992 | B1* | 12/2009 | Dolly et al. | 424/197.11 |
| 7,785,606 | B2* | 8/2010 | Ichtchenko et al. | 424/234.1 |
| 8,044,188 | B2* | 10/2011 | Ichtchenko et al. | 536/23.7 |
| 2003/0219462 | A1* | 11/2003 | Steward et al. | 424/239.1 |
| 2004/0013687 | A1 | 1/2004 | Simpson et al. | |
| 2004/0219637 | A1* | 11/2004 | Williams | 435/69.3 |
| 2004/0220100 | A1 | 11/2004 | Waugh et al. | |
| 2004/0265935 | A1* | 12/2004 | Atassi | 435/7.32 |
| 2005/0106182 | A1* | 5/2005 | Li et al. | 424/239.1 |
| 2006/0100149 | A1* | 5/2006 | O'Mahony et al. | 514/12 |
| 2006/0204524 | A1* | 9/2006 | Ichtchenko et al. | 424/239.1 |
| 2006/0258846 | A1* | 11/2006 | Breidenbach et al. | 530/350 |
| 2007/0299008 | A1* | 12/2007 | Rummel | 514/12 |
| 2009/0311275 | A1* | 12/2009 | Rummel et al. | 424/179.1 |

FOREIGN PATENT DOCUMENTS

| | | |
|---|---|---|
| WO | WO 94/10300 | 11/1994 |
| WO | WO 01/27152 A2 * | 4/2001 |
| WO | WO 01/27154 A2 * | 4/2001 |

OTHER PUBLICATIONS

Yang et al (11th Annual Sigma Xi Research Exhibit, University of Massachusetts, Dartmouth, MA Apr. 26-27, 2005).*
Agarwal et al., (2005) Biochemistry 44, 8291-8302.
D'Argenio et al, 1997. ADAPT II User's Guide, Biomedical Simulations Resource, University of Southern California, Los Angeles.
Arnon S., J. Infect. Dis. 154:201-206 (1986).
Arnon, S., Ann. Rev. Med. 31:541 (1980).
Arnon S., Epidemiol. Rev. 3:45 (1981).
Ausubel et al., eds. Current Protocols in Molecular Biology 1999, J. Wiley: New York.
Balady, M., USAMRDC Newsletter, p. 6 (1991).
Balsari et al., Anticancer Res. 10:129-132 (1990).
Bartel et al., Biotechniques 14:920 924 [1993].
Binz et al., (2002) Biochemistry 41, 1717-1723.
Cai et al., (1999) Biochemistry 38, 6903-6910.
Carrell et al., Angew. Chem. Int. Ed. Engl. 33.2059 [1994].
Carell et al., Angew. Chem. Int. Ed. Engl. 33:2061 [1994].
Chaddock et al., (2002) Trends Biochem. Sci. 27, 552-558.
Charles et al., Infect. Immun. 59:1627 (1991).
Cho et al., Science 261:1303 [1993].
Cull et al., Proc. Nad. Acad. Sci. USA 89:18651869 [1992].
Cwirla et al., Proc. NatI. Acad. Sci. 87:6378 6382 [1990].
DasGupta et al., Biochem. Biophys. Res. Commun. 48:108 (1972).
DasGupta, J. Physiol. 84:220 (1990).
Devlin Science 249:404 406 [1990].
DeWitt et al., Proc. Natl. Acad. Sci. U.S.A. 90:6909 [1993].
Erb et al., Proc. Nad. Acad. Sci. USA 91:11422 [1994].
Federal Reg., 38, 26130 (1980).
Felici, J. Mol. Biol. 222:301 [1991].
Fodor, Nature 364:555 556 [1993].
Frankovich, T.L. and Arnon, S., West. J. Med. 154:103 (1991).
Franz, D. R. et al., in Botulinum and Tetanus Neurotoxins, B.R. DasGupta, ed., Plenum Press, New York (1993), pp. 473-476.
Gallop et al., J. Med. Chem. 37:1233 [1994].
Hage and Tweed J. Chromatogr. Biomed. Sci. Appl 699:499 525 [1997].
Halpern et al., Infect. Immun. 58:1004 (1990).
Hatheway, C. L., Clin. Microbiol. Rev. 3:66-98 (1990).
Heegaard J. Mol. Recognit 11: 141 8 [1998].
Holzer, E., Med. Klin. 41:1735 (1962).
Houghten, Biotechniques 13:412 421 [1992].
Hunter, et al, J. Immunol., 129:1165-1172 (1982).
Int. J. Cancer 42:798-802 (1988), Balsari et al.
Iwabuchi et al., Oncogene 8:1693 1696 [1993].
Krieglstein et al., J. Protein Chem. 13, 49-57.
Kukreja et al., "Immunological characterization of the subunits of type A botulinum neurotoxin and different components of its associated proteins", Toxicon 53 (2009), 616-624.
Kukreja et al, "The role of two active site Glu residules in the molecular action of botulinum neurotoxin endopeptidase", Biochimica et Biophysica Acta 1774, (2007), 213-222.
Lacy et al., (1998) Nat Struct Biol. 5, 898-902.
Lam, Nature 354:82 84 [1991].
Lam (1997) AntiBoNT/A Drug Des. 12:145.
LaPenotiere, H.F., et al., In: Botulinum and Tetanus Neurotoxins, B.R. DasGupta, ed., Plenum Press, New York (1993), p. 463.
Li et al., (2000) Biochemistry 39, 2399-2405.
Li and Singh (2000) Biochemistry 39, 6466-6474.
Li and Singh, B.R. (1999) Toxin Rev. 18, 95-112.
MacDonald, K.L., et al., Am. J. Epidemiol. 124:794 (1986).
Macdougall et al., Clin. Pharmacokinet. 20:99-113 (1991).
Madura et al., J. Biol. Chem. 268.12046 12054 [1993].
Makoff et al., Bio/Technology 7:1043 (1989).
Makoff et al., Nucleic Acids Res. 17:10191 (1989).
McConnell et al. Science 257:1906 1912 [1992].
Miller et al., Degradation Rates of Oral Resorbable Implants {Polylactates and Polyglycolates: Rate Modification and Changes in PLA/PGA Copolymer Ratios, J. Biomed. Mater. Res., vol. II: 711-719 (1977).
Moberg et al., Appl. Environ. Microbiol. 35:878 (1978).
Montecucco and Schiavo, (1995) Q. Rev. Biophys, 28,423-472.
Montecucco and Schiavo, G (1993) Trends Biochem. Sci. 18, 324-327.
Perason, F.C., Pyrogens: endotoxins, LAL testing and depyrogenation, Marcel Dekker, New York, (1985), pp. 150-155.
Popoff et al., Infect. Immun. 59:3673 (1991).
Rigoni et al., Biochemistry and Biophys, Res. Commun 288, 1231-1237, 2001.
Rivas and Minton, Trends Biochem Sci 18:284 7 [1993].
Romanos et al., Nucleic Acids Res. 19:1461 (1991).
Rossetto et al., (2001) Toxicon 39, 1150-1159.
Sakaguchi, F., G., Pharmac. Ther. 19:165 (1983).
Schantz et al., Microbiol. Rev. 56:80 (1992).
Schiavo, G., Matteoli, M., and Montecucco (2000) Physio. Rev. 80, 717-755.
Schwarz, P.J., and S.S. Arnon, Western J. Med. 156:197 (1992).
Scott et al., Improving Protein Therapeutics With Sustained Release Formulations, Nature Biotechnology, vol. 16:153-157 (1998).
Scott and Smith, Science 249:386 390 [1990].
Sharma and Singh (2004) Biochemistry 43, 4791-4798.
Sharma and Singh (1998) Journal of Natural Toxins 7, No. 3 239-253.
Singh et al., 2010.
Sjolander and Urbaniczky, Anal. Chem. 63:2338 2345 [1991].
Sneath, P.H.A., et al., "Clostridium," Bergey's Manual of Systematic Bacteriology, vol. 2, pp. 1141-1200, Williams & Wilkins (1986).
Sugiyama, H., Microbiol. Rev. 44:419 (1980).
Swartz, M.N., "Anaerobic Spore-Forming Bacilli: The Clostridia," pp. 633-646, in B.D. Davis et al., (eds.), Microbiology, 4th edition, J.B. Lippincott Co. (1990).
Sollner et al., (1993) Nature 362, 318-324.
Szabo et al. Curr. Opin. Struct. Biol. 5:699 705 [1995].
Tacket, C.O., et al., Am. J. Med. 76:794 (1984).
Thalley et al., In: Botulinum and Tetanus Neurotoxins, B.R. DasGupta, ed., Plenum Press, New York (1993), p. 467.
Thompson et al., Eur. J. Biochem. 189:73 (1990).
United States Pharmacopeia, vol. XXII (1990) United States Pharmacopeial Convention, Rockville, MD, p. 151.
Zervos et al., Cell 72:223 232 [1993].
Zhang et al., 2009.
Zuckermann et al., J. Med. Chem. 37: 2678 [1994].
PCT The International Search Report and the Written Opinion of the International Searching Authority, Jun. 1, 2009.

* cited by examiner

Marker size     1    2    3

133kDa →

78kDa →

45kDa →
33kDa →

Lane1 DrBoNT
Lane2 Kaleidoscope prestained Marker
Lane3 Native Toxin

FIGURE 1

Lane 1: Low Molecular Weight Standard

Lane 2: E224A/E262A Botulinum Neurotoxin A

Lane 3: Native Botulinum Neurotoxin A

FIGURE 2

Dr BoNT vs Native Toxin far UV CD

Gel Screening for Dr BoNT/A

Vector+mmLC 4.8kb
HC with partially LC 3kb 1  2  3  4  5  6  7  8  9  10

FIGURE 7

DrBoNT/A BINDING TO SH-SY5Y CELLS AT 4°C FOR 1 HOUR

SEQUENCE LISTING

<160> NUMBER OF SEQ ID NOS: 14

<210> SEQ ID NO 1
<211> LENGTH: 43
<212> TYPE: DNA
<213> ORGANISM: Artificial Sequence
<220> FEATURE:
<223> OTHER INFORMATION: Synthetic

<400> SEQUENCE: 1
ggccgccccg ggcgataaat atagtaccta aggtaaatta cac         43

<210> SEQ ID NO 2
<211> LENGTH: 91
<212> TYPE: DNA
<213> ORGANISM: Artificial Sequence
<220> FEATURE:
<223> OTHER INFORMATION: Synthetic

<400> SEQUENCE: 2
aaattataat aaactgcagg ccttagtgat ggtgatggtg atgcccggga gttggcgggg    60
ccttcagtgg cctttctccc catccatcat c                                   91

```
<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
cataaccatt tcgcgtaaga ttca                                          24

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
ttgaccatta aagtttgctg cta                                           23

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
actaattgtt ctacccagcc taaa                                          24

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
tgttccatta tcttcgtgct ca                                            22

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
aagaaatgaa aaatgggatg aggt                                          24

<210> SEQ ID NO 8
<211> LENGTH: 23
<212> TYPE: DNA
<213> ORGANISM: Artificial Sequence
<220> FEATURE:
<223> OTHER INFORMATION: Synthetic

<400> SEQUENCE: 8
aacggttaga agattttgat gct                                           23

<210> SEQ ID NO 9
<211> LENGTH: 24
<212> TYPE: DNA
<213> ORGANISM: Artificial Sequence
<220> FEATURE:
<223> OTHER INFORMATION: Synthetic
```

```
<400> SEQUENCE: 9
tggactttac aggatactca ggaa                                          24

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
gcatcacagg caggcgtaga                                               20

<210> SEQ ID NO 11
<211> LENGTH: 38
<212> TYPE: DNA
<213> ORGANISM: Artificial Sequence
<220> FEATURE:
<223> OTHER INFORMATION: Synthetic

<400> SEQUENCE: 11
ccggcagtaa ctctggcaat ggccctcatc cacgctgg                           38

<210> SEQ ID NO 12
<211> LENGTH: 38
<212> TYPE: DNA
<213> ORGANISM: Artificial Sequence
<220> FEATURE:
<223> OTHER INFORMATION: Synthetic

<400> SEQUENCE: 12
ccagcgtgga tgagggccat tgccagagtt actgccgg                           38

<210> SEQ ID NO 13
<211> LENGTH: 44
<212> TYPE: DNA
<213> ORGANISM: Artificial Sequence
<220> FEATURE:
<223> OTHER INFORMATION: Synthetic

<400> SEQUENCE: 13
ccggcagtaa ctctggcaat ggccctcatc caagctggtc accg                    44

<210> SEQ ID NO 14
<211> LENGTH: 38
<212> TYPE: DNA
<213> ORGANISM: Artificial Sequence
<220> FEATURE:
<223> OTHER INFORMATION: Synthetic

<400> SEQUENCE: 14
cggtgaccag cttggatgag ggccattgcc agagttac                           38
```

DETOXIFIED RECOMBINANT BOTULINUM NEUROTOXIN

This application for patent under 35 U.S.C.§111(a) claims priority to Provisional Application(s) Ser. No. 60/994,603 filed on Sep. 20, 2007 under 35 U.S.C. §111(b).

STATEMENT OF GOVERNMENT INTEREST

This invention was supported by Grant number DAMD17-02-C-001 awarded by the U.S. Army Medical Research and Material Command and Grant number AI057159-01 awarded by the National Institutes of Health. The government has certain rights in the invention.

FIELD OF THE INVENTION

The present invention relates to the isolation, detection, and use of *Clostridium botulinum* neurotoxin derived amino acid and nucleic acid sequences. In one embodiment, the nucleic acids are mutated to create a recombinant detoxified botulinum neurotoxin. In one embodiment, the detoxified neurotoxin is used as a vaccine. In one embodiment, the detoxified neurotoxin is used as a botulinum inhibitor and/or antidote. In one embodiment, the detoxified neurotoxin is used to either detect botulinum intoxication or screen for compounds effective in inhibiting botulinum toxicity.

BACKGROUND OF THE INVENTION

The genus *Clostridium* is comprised of gram-positive, anaerobic, spore-forming bacilli. The natural habitat of these organisms is the environment and the intestinal tracts of humans and other animals. Indeed, clostridia are ubiquitous; they are commonly found in soil, dust, sewage, marine sediments, decaying vegetation, and mud. See e.g., P. H. A. Sneath et al., "*Clostridium*," Bergey's Manual of Systematic Bacteriology, Vol. 2, pp. 1141-1200, Williams & Wilkins (1986). Despite the identification of approximately 100 species of *Clostridium*, only a small number have been recognized as etiologic agents of medical and veterinary importance. Nonetheless, these species are associated with very serious diseases, including botulism, tetanus, anaerobic cellulitis, gas gangrene, bacteremia, pseudomembranous colitis, and clostridial gastroenteritis.

Several strains of *Clostridium botulinum* produce toxins of significance to human and animal health. C. L. Hatheway, Clin. Microbiol. Rev. 3:66-98 (1990). The effects of these toxins range from diarrheal diseases that can cause destruction of the colon, to paralytic effects that can cause death. Particularly at risk for developing clostridial diseases are neonates and humans and animals in poor health (e.g., those suffering from diseases associated with old age or immunodeficiency diseases).

What is needed is an effective therapy against botulism that is free of dangerous side effects, is available in large supply at a reasonable price, and can be safely and gently delivered so that prophylactic application to infants is feasible. Safe and effective vaccine preparations for administration to those at risk of exposure to *C. botulinum* toxins are also needed.

SUMMARY OF THE INVENTION

The present invention relates to the isolation, detection, and use of *Clostridium botulinum* neurotoxin derived amino acid and nucleic acid sequences. In one embodiment, the nucleic acids are mutated to create a recombinant detoxified botulinum neurotoxin. In one embodiment, the detoxified neurotoxin is used as a vaccine. In one embodiment, the detoxified neurotoxin is used as a botulinum inhibitor and/or antidote. In one embodiment, the detoxified neurotoxin is used to either detect botulinum intoxication or screen for compounds effective in inhibiting botulinum toxicity.

In one embodiment, the present invention contemplates a composition comprising a non-toxic recombinant botulinum protein. In one embodiment, the protein comprises a double mutant botulinum toxin L chain. In one embodiment, the double mutant comprises E224A/E262A. In one embodiment, the protein comprises a triple mutant botulinum toxin L chain. In one embodiment, the protein comprises a quadruple mutant botulinum toxin L chain. In one embodiment, the protein comprises a botulinum toxin H chain. In one embodiment, the composition is a botulism vaccine. In one embodiment, the composition is a botulism antidote.

In one embodiment, the present invention contemplates an isolated nucleic acid sequence encoding a double mutant botulinum light chain and a botulinum heavy chain. In one embodiment, the nucleic acid sequence is ligated to a vector. In one embodiment, the vector comprises a pBN3 vector. In one embodiment, the vector is transfected into a host cell. In one embodiment, the host cell comprises an *E. coli* cell. In one embodiment, the light chain double mutant comprises E224A/E262A.

In one embodiment, the present invention contemplates an isolated nucleic acid sequence encoding a triple mutant botulinum light chain and a botulinum heavy chain. In one embodiment, the nucleic acid sequence is ligated to a vector. In one embodiment, the vector comprises a pBN3 vector. In one embodiment, the vector is transfected into a host cell. In one embodiment, the host cell comprises an *E. coli* cell.

In one embodiment, the present invention contemplates an isolated nucleic acid sequence encoding a quadruple mutant botulinum light chain and a botulinum heavy chain. In one embodiment, the nucleic acid sequence is ligated to a vector. In one embodiment, the vector comprises a pBN3 vector. In one embodiment, the vector is transfected into a host cell. In one embodiment, the host cell comprises an *E. coli* cell.

In one embodiment, the present invention contemplates a method comprising: a) providing; i) a subject at risk for developing botulism; and ii) a composition comprising a non-toxic recombinant botulinum protein; and b) administering the composition to the subject under conditions such that botulism development is reduced and/or prevented. In one embodiment, the protein comprises a botulism vaccine. In one embodiment, the vaccine comprises a double mutant botulinum light chain. In one embodiment, the light chain double mutant comprises E224A/E262A. In one embodiment, the protein comprises a triple mutant botulinum toxin L chain. In one embodiment, the protein comprises a quadruple mutant botulinum toxin L chain.

In one embodiment, the administering is selected from the group consisting of oral, topical, and/or intraperitoneal. In one embodiment, the administering comprises parenteral administration. In one embodiment, the parenteral administration is selected from the group consisting of intravenous, intraarterial, subcutaneous, intraperitoneal or intramuscular injection or infusion; or intracranial, intrathecal or intraventricular, administration. In one embodiment, the composition further comprises a liposome, wherein the protein is encapsulated within the liposome. In one embodiment, the liposome is targeted to a disease tissue or cell.

In one embodiment, the present invention contemplates a method comprising: a) providing; i) a subject having at least one symptom of botulism; and ii) a composition comprising a non-toxic recombinant botulinum protein; and b) administering the composition to the subject under conditions such that the at least one symptom of botulism is reduced and/or prevented. In one embodiment, the protein comprises a botulism antidote. In one embodiment, the antidote comprises a double mutant botulinum light chain. In one embodiment, the light chain double mutant comprises E224A/E262A. In one embodiment, the protein comprises a triple mutant botulinum toxin L chain. In one embodiment, the protein comprises a quadruple mutant botulinum toxin L chain. In one embodiment, the administering is selected from the group consisting of oral, topical, and/or intraperitoneal. In one embodiment, the administering comprises parenteral administration. In one embodiment, the parenteral administration is selected from the group consisting of intravenous, intraarterial, subcutaneous, intraperitoneal or intramuscular injection or infusion; or intracranial, intrathecal or intraventricular, administration. In one embodiment, the composition further comprises a liposome, wherein the protein is encapsulated within the liposome. In one embodiment, the liposome is targeted to a diseased tissue or cell. In one embodiment, the protein is delivered into intracellular space of said cell. In one embodiment, the cell comprises a neuronal cell. In one embodiment, the cell comprises an epithelial cell.

In one embodiment, the present invention contemplates a drug delivery system comprising a composition comprising a non-toxic recombinant botulinum protein attached to a carrier. In one embodiment, the drug delivery system further comprises a medical device capable of administering the composition to a diseased tissue. In one embodiment, the carrier comprises a liposome. In one embodiment, the carrier comprises a microparticle. In one embodiment, the protein comprises a non-toxic recombinant botulinum L chain protein. In one embodiment, the L chain protein comprises a double mutation. In one embodiment, the double mutation comprises E224A/E262A. In one embodiment, the protein comprises a triple mutant botulinum toxin L chain. In one embodiment, the protein comprises a quadruple mutant botulinum toxin L chain. In one embodiment, the medical device includes, but is not limited to, a catheter, a sprayer, and/or a tube. In one embodiment, the carrier further comprises a drug. In one embodiment, the drug is effective against botulism and/or secondary considerations thereof. In one embodiment, the drug includes, but is not limited to, antiinflammatory, corticosteroid, antithrombotic, antibiotic, antifungal, antiviral, analgesic and anesthetic drugs. In one embodiment, the drug includes, but is not limited to, peptides, proteins, polypeptides and/or fragments thereof. In one embodiment, the drug includes, but is not limited to, nucleic acids, polynucleic acids and/or fragments thereof. In one embodiment, the nucleic acid comprises silencing RNA (siRNA). In one embodiment, the nucleic acid comprises interfering RNA (RNAi). In one embodiment, the polynucleic acid comprises a sense nucleic acid sequence. In one embodiment, the polynucleic acid comprises an antisense nucleic acid sequence.

In one embodiment, the present invention contemplates a method comprising: a) providing; i) a subject in desire of a botulinum pharmacokinetic analysis; and ii) a composition comprising a non-toxic recombinant botulinum protein; and b) administering the composition to the subject under conditions to perform a pharmacokinetic analysis. In one embodiment, the protein comprises a double mutant botulinum L chain. In one embodiment, the L chain double mutant comprises E224A/E262A. In one embodiment, the protein comprises a triple mutant botulinum toxin L chain. In one embodiment, the protein comprises a quadruple mutant botulinum toxin L chain. In one embodiment, the pharmacokinetic analysis comprises measurement of total body amount. In one embodiment, the pharmacokinetic analysis comprises measurement of maximal elimination rate. In one embodiment, the pharmacokinetic analysis comprises measurement of half-maximal elimination rate. In one embodiment, the pharmacokinetic analysis comprises measurement of a volume of distribution. In one embodiment, the pharmacokinetic analysis comprises a concentration-time profile. In one embodiment, the pharmacokinetic analysis comprises a compartment model fitting analysis.

In one embodiment, the present invention contemplates a cell culture comprising a plurality of cells having a nucleic acid sequence encoding a botulinum toxin protein. In one embodiment, the nucleic acid sequence encodes a wild type botulinum toxin protein. In one embodiment, the nucleic acid sequence encodes a double mutant BoNT/A protein. In one embodiment, the nucleic acid sequence encodes a triple mutant BoNT/A protein. In one embodiment, the nucleic acid sequence encodes a quadruple mutant BoNT/A protein. In one embodiment, the cell culture comprises E. coli cells. In one embodiment, the cell culture overexpresses the botulinum protein.

DEFINITIONS

To facilitate understanding of the invention, a number of terms are defined below.

As used herein, the term "neutralizing" is used in reference to antitoxins, particularly antitoxins comprising antibodies, which have the ability to prevent the pathological actions of the toxin against which the antitoxin is directed.

As used herein, the term "overproducing" is used in reference to the production of clostridial toxin polypeptides in a host cell and indicates that the host cell is producing more of the clostridial toxin by virtue of the introduction of nucleic acid sequences encoding said clostridial toxin polypeptide than would be expressed by said host cell absent the introduction of said nucleic acid sequences. To allow ease of purification of toxin polypeptides produced in a host cell it is preferred that the host cell express or overproduce said toxin polypeptide at a level greater than 1 mg/liter of host cell culture.

As used herein, the term "fusion protein" refers to a chimeric protein containing the protein of interest (i.e., for example, C. difficile toxin A or B and fragments thereof) joined to an exogenous protein fragment (the fusion partner which consists of a non-toxin protein). The fusion partner may enhance solubility of the C. difficile protein as expressed in a host cell, may provide an affinity tag to allow purification of the recombinant fusion protein from the host cell or culture supernatant, or both. If desired, the fusion protein may be removed from the protein of interest (i.e., toxin protein or fragments thereof) prior to immunization by a variety of enzymatic or chemical means known to the art.

As used herein the term "non-toxin protein" or "non-toxin protein sequence" refers to that portion of a fusion protein which comprises a protein or protein sequence which is not derived from a bacterial toxin protein.

The term "protein of interest" as used herein refers to the protein whose expression is desired within the fusion protein. In a fusion protein the protein of interest will be joined or fused with another protein or protein domain, the fusion partner, to allow for enhanced stability of the protein of interest and/or ease of purification of the fusion protein.

As used herein, the term "maltose binding protein" refers to the maltose binding protein of E. coli. A portion of the maltose binding protein may be added to a protein of interest to generate a fusion protein; a portion of the maltose binding protein may merely enhance the solubility of the resulting fusion protein when expressed in a bacterial host. On the other hand, a portion of the maltose binding protein may allow affinity purification of the fusion protein on an amylose resin.

As used herein, the term "poly-histidine tract" when used in reference to a fusion protein refers to the presence of two to ten histidine residues at either the amino- or carboxy-terminus of a protein of interest. A poly-histidine tract of six to ten residues is preferred. The poly-histidine tract is also defined functionally as being a number of consecutive histidine residues added to the protein of interest which allows the affinity purification of the resulting fusion protein on a nickel-chelate column.

As used herein, the term "purified" or "to purify" refers to the removal of contaminants from a sample. For example, antitoxins are purified by removal of contaminating non-immunoglobulin proteins; they are also purified by the removal of immunoglobulin that does not bind toxin. The removal of non-immunoglobulin proteins and/or the removal of immunoglobulins that do not bind toxin results in an increase in the percent of toxin-reactive immunoglobulins in the sample. In another example, recombinant toxin polypeptides are expressed in bacterial host cells and the toxin polypeptides are purified by the removal of host cell proteins; the percent of recombinant toxin polypeptides is thereby increased in the sample. Additionally, the recombinant toxin polypeptides are purified by the removal of host cell components such as lipopolysaccharide (e.g., endotoxin).

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein refers to a protein which is isolated from a natural source as opposed to the production of a protein by recombinant means.

As used herein the term "portion" when in reference to a protein (as in "a portion of a given protein") refers to fragments of that protein. The fragments may range in size from four amino acid residues to the entire amino acid sequence minus one amino acid.

As used herein "soluble" when in reference to a protein produced by recombinant DNA technology in a host cell is a protein which exists in solution in the cytoplasm of the host cell; if the protein contains a signal sequence the soluble protein is exported to the periplasmic space in bacteria hosts and is secreted into the culture medium in eukaryotic cells capable of secretion or by bacterial host possessing the appropriate genes (i.e., the kil gene). In contrast, an insoluble protein is one which exists in denatured form inside cytoplasmic granules (called an inclusion bodies) in the host cell. High level expression (i.e., greater than 10-20 mg recombinant protein/liter of bacterial culture) of recombinant proteins often results in the expressed protein being found in inclusion bodies in the bacterial host cells. A soluble protein is a protein which is not found in an inclusion body inside the host cell or is found both in the cytoplasm and in inclusion bodies and in this case the protein may be present at high or low levels in the cytoplasm.

A distinction is drawn between a soluble protein (i.e., a protein which when expressed in a host cell is produced in a soluble form) and a "solubilized" protein. An insoluble recombinant protein found inside an inclusion body may be solubilized (i.e., rendered into a soluble form) by treating purified inclusion bodies with denaturants such as guanidine hydrochloride, urea or sodium dodecyl sulfate (SDS). These denaturants must then be removed from the solubilized protein preparation to allow the recovered protein to renature (refold). Not all proteins will refold into an active conformation after solubilization in a denaturant and removal of the denaturant. Many proteins precipitate upon removal of the denaturant. SDS may be used to solubilize inclusion bodies and will maintain the proteins in solution at low concentration. However, dialysis will not always remove all of the SDS (SDS can form micelles which do not dialyze out); therefore, SDS-solubilized inclusion body protein is soluble but not refolded.

A distinction is drawn between proteins which are soluble (i.e., dissolved) in a solution devoid of significant amounts of ionic detergents (e.g., SDS) or denaturants (e.g., urea, guanidine hydrochloride) and proteins which exist as a suspension of insoluble protein molecules dispersed within the solution. A soluble protein will not be removed from a solution containing the protein by centrifugation using conditions sufficient to remove bacteria present in a liquid medium (i.e., centrifugation at 5,000×g for 4-5 minutes). For example, to test whether two proteins, protein A and protein B, are soluble in solution, the two proteins are placed into a solution selected from the group consisting of PBS-NaCl (PBS containing 0.5 M NaCl), PBS-NaCl containing 0.2% Tween 20, PBS, PBS containing 0.2% Tween 20, PBS-C (PBS containing 2 mM $CaCl_2$), PBS-C containing either 0.1 or 0.5% Tween 20, PBS-C containing either 0.1 or 0.5% NP-40, PBS-C containing either 0.1 or 0.5% Triton X-100, PBS-C containing 0.1% sodium deoxycholate. The mixture containing proteins A and B is then centrifuged at 5000×g for 5 minutes. The supernatant and pellet formed by centrifugation are then assayed for the presence of protein A and B. If protein A is found in the supernatant and not in the pellet except for minor amounts (i.e., less than 10%) as a result of trapping, protein is said to be soluble in the solution tested. If the majority of protein B is found in the pellet (i.e., greater than 90%), then protein B is said to exist as a suspension in the solution tested.

As used herein, the term "therapeutic amount" refers to that amount of antitoxin required to neutralize the pathologic effects of one or more clostridial toxins in a subject.

The term "pyrogen" as used herein refers to a fever-producing substance. Pyrogens may be endogenous to the host (e.g., prostaglandins) or may be exogenous compounds (e.g., bacterial endo- and exotoxins, nonbacterial compounds such as antigens and certain steroid compounds, etc.). The presence of pyrogen in a pharmaceutical solution may be detected using the U.S. Pharmacopeia (USP) rabbit fever test (United States Pharmacopeia, Vol. XXII (1990) United States Pharmacopeial Convention, Rockville, Md., p. 151).

The term "endotoxin" as used herein refers to the high molecular weight complexes associated with the outer membrane of gram-negative bacteria. Unpurified endotoxin contains lipids, proteins and carbohydrates. Highly purified endotoxin does not contain protein and is referred to as lipopolysaccharide (LPS). Because unpurified endotoxin is of concern in the production of pharmaceutical compounds (e.g., proteins produced in *E. coli* using recombinant DNA technology), the term endotoxin as used herein refers to unpurified endotoxin. Bacterial endotoxin is a well known pyrogen.

As used herein, the term "endotoxin-free" when used in reference to a composition to be administered parenterally (with the exception of intrathecal administration) to a host means that the dose to be delivered contains less than 5 EU/kg body weight FDA Guidelines for Parenteral Drugs (December 1987). Assuming a weight of 70 kg for an adult human, the dose must contain less than 350 EU to meet FDA Guidelines for parenteral administration. Endotoxin levels are measured herein using the *Limulus Amebocyte* Lysate (LAL) test (*Limulus Amebocyte* Lysate Pyrochrome™, Associates of Cape Cod, Inc. Woods Hole, Mass.). To measure endotoxin levels in preparations of recombinant proteins, 0.5 ml of a solution comprising 0.5 mg of purified recombinant protein in 50 mM NaPO$_4$, pH 7.0, 0.3M NaCl and 10% glycerol is used in the LAL assay according to the manufacturer's instructions for the endpoint chromogenic without diazo-coupling method. Compositions containing greater than or equal less than 60 endotoxin units (EU)/mg of purified recombinant protein are herein defined as "substantially endotoxin-free." Typically, administration of bacterial toxins or toxoids to adult humans for the purpose of vaccination involves doses of about 10-500 μg protein/dose. Therefore, administration of 10-500 μg of a purified recombinant protein to a 70 kg human, wherein said purified recombinant protein preparation contains 60 EU/mg protein, results in the introduction of only 0.6 to 30 EU (i.e., 0.2 to 8.6% of the maximum allowable endotoxin burden per parenteral dose).

The LAL test is accepted by the U.S. FDA as a means of detecting bacterial endotoxins (21 C.F.R. §§660.100-105). Studies have shown that the LAL test is equivalent or superior to the USP rabbit pyrogen test for the detection of endotoxin and thus the LAL test can be used as a surrogate for pyrogenicity studies in animals F. C. Perason, Pyrogens: endotoxins, LAL testing and depyrogenation, Marcel Dekker, New York (1985), pp. 150-155. The FDA Bureau of Biologics accepts the LAL assay in place of the USP rabbit pyrogen test so long as the LAL assay utilized is shown to be as sensitive as, or more sensitive as the rabbit test Fed. Reg., 38, 26130 (1980).

The term "monovalent" when used in reference to a clostridial vaccine refers to a vaccine which is capable of provoking an immune response in a host animal directed against a single type of clostridial toxin. For example, if immunization of a host with *C. botulinum* type A toxin vaccine induces antibodies in the immunized host which protect against a challenge with type A toxin but not against challenge with type B, C, D, E, or F toxins, then the type A vaccine is said to be monovalent. In contrast, a "multivalent" vaccine provokes an immune response in a host animal directed against several (i.e., more than one) clostridial toxins. For example, if immunization of a host with a vaccine comprising *C. botulinum* type A and B toxins induces the production of antibodies which protect the host against a challenge with both type A and B toxin, the vaccine is said to be multivalent (in particular, this hypothetical vaccine is bivalent).

As used herein the term "immunogenically-effective amount" refers to that amount of an immunogen required to invoke the production of protective levels of antibodies in a host upon vaccination.

The term "protective level", when used in reference to the level of antibodies induced upon immunization of the host with an immunogen which comprises a bacterial toxin, means a level of circulating antibodies sufficient to protect the host from challenge with a lethal dose of the toxin.

As used herein the terms "protein" and "polypeptide" refer to compounds comprising amino acids joined via peptide bonds and are used interchangeably.

The terms "toxin" and "neurotoxin" when used in reference to toxins produced by members (i.e., species and strains) of the genus *Clostridium* are used interchangeably and refer to the proteins which are poisonous to nerve tissue.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 presents exemplary Western Blot data showing anti-BoNT/A antibody binding to either DR BoNT/A protein (Lane 1) or native BoNT/A protein (Lane 3). Kaleidoscope prestained marker standard was used for visualization (Lane 2).

FIG. 2 presents exemplary SDS-PAGE electrophoresis data showing the approximate molecular weights of DR BoNT/A (Lane 2) and native BoNT/A (Lane 3).

FIG. 3 presents exemplary circular dichroism data showing absorption maxima at 208 and 222 nm for both DR BoNT/A protein and native BoNT/A protein.

Figure 4:
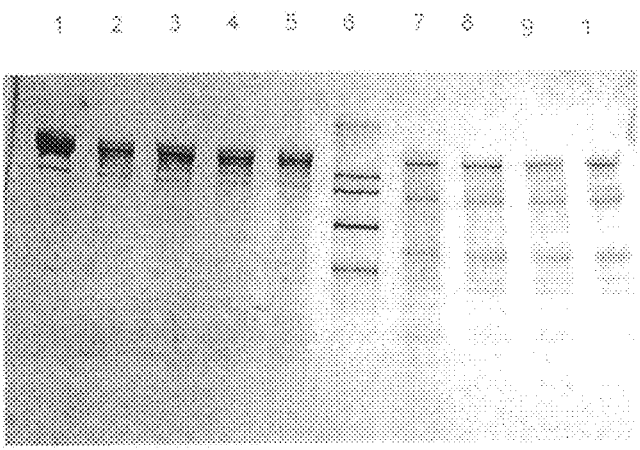
FIG. 4 presents exemplary trypsinization fragmentation patterns of native BoNT/A protein under reducing and non-reducing conditions.

| Lane 1 | Tripsin digest 0 min as control |
| --- | --- |
| Lane 2 | Tripsin digest 5 min boiled with SDS non-reducing Bf |
| Lane 3 | Tripsin digest 10 min boiled with SDS non-reducing Bf |
| Lane 4 | Tripsin digest 30 min boiled with SDS non-reducing Bf |
| Lane 5 | Tripsin digest 60 min boiled with SDS non-reducing Bf |
| Lane 6 | High MW marker (top to bottom 200, 116, 97, 66, 45 KD) |
| Lane 7 | Tripsin digest 5 min boiled with SDS reducing Bf |
| Lane 8 | Tripsin digest 10 min boiled with SDS reducing Bf |
| Lane 9 | Tripsin digest 30 min boiled with SDS reducing Bf |
| Land 10 | Tripsin digest 60 min boiled with SDS reducing Bf |

Figure 5:
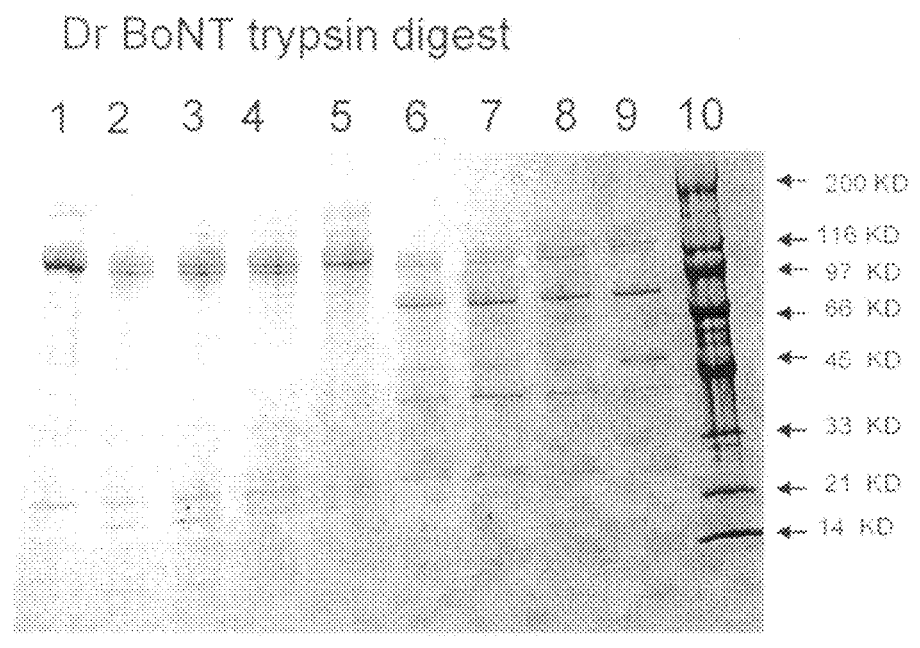

FIG. 5 presents exemplary trypsinization fragmentation patterns of DR BoNT/A protein under reducing and non-reducing conditions.

| Lane 1 | Tripsin digestion/0 min |
| --- | --- |
| Lane 2 | Tripsin digestion/5 min non-reducing condition |
| Lane 3 | Tripsin digestion/10 min non-reducing condition |
| Lane 4 | Tripsin digestion/30 min non-reducing condition |
| Lane 5 | Tripsin digestion/60 min non-reducing condition |
| Lane 6 | Tripsin digestion/5 min reducing condition |
| Lane 7 | Tripsin digestion/10 min reducing condition |
| Lane 8 | Tripsin digestion/30 min reducing condition |
| Lane 9 | Tripsin digestion/60 min reducing condition |
| Land 10 | High and Low molecular standard mixture from Bio-rad |

Figure 6:
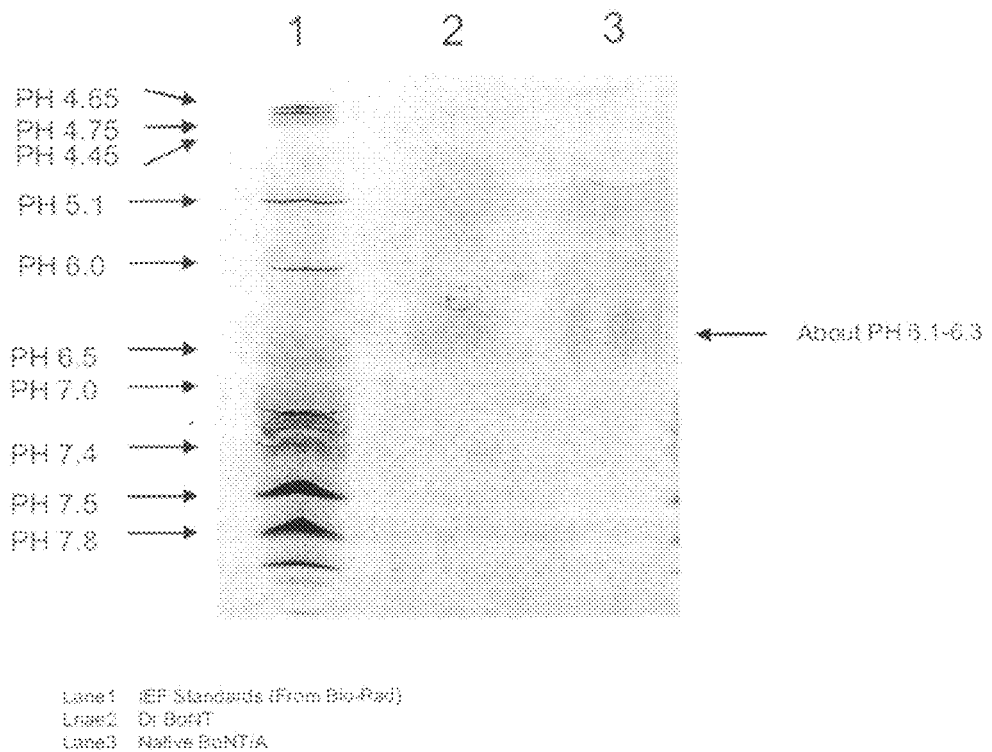

FIG. 6 presents exemplary isoelectric focusing data showing approximate pI's for either DR BoNT/A (Lane 2) and native BoNT/A (Lane 3).

FIG. 7 presents exemplary data showing the integration of BoNT/A heavy chain (HC) into a pBN3 vector double mutant light chain (LC).

Figure 8:
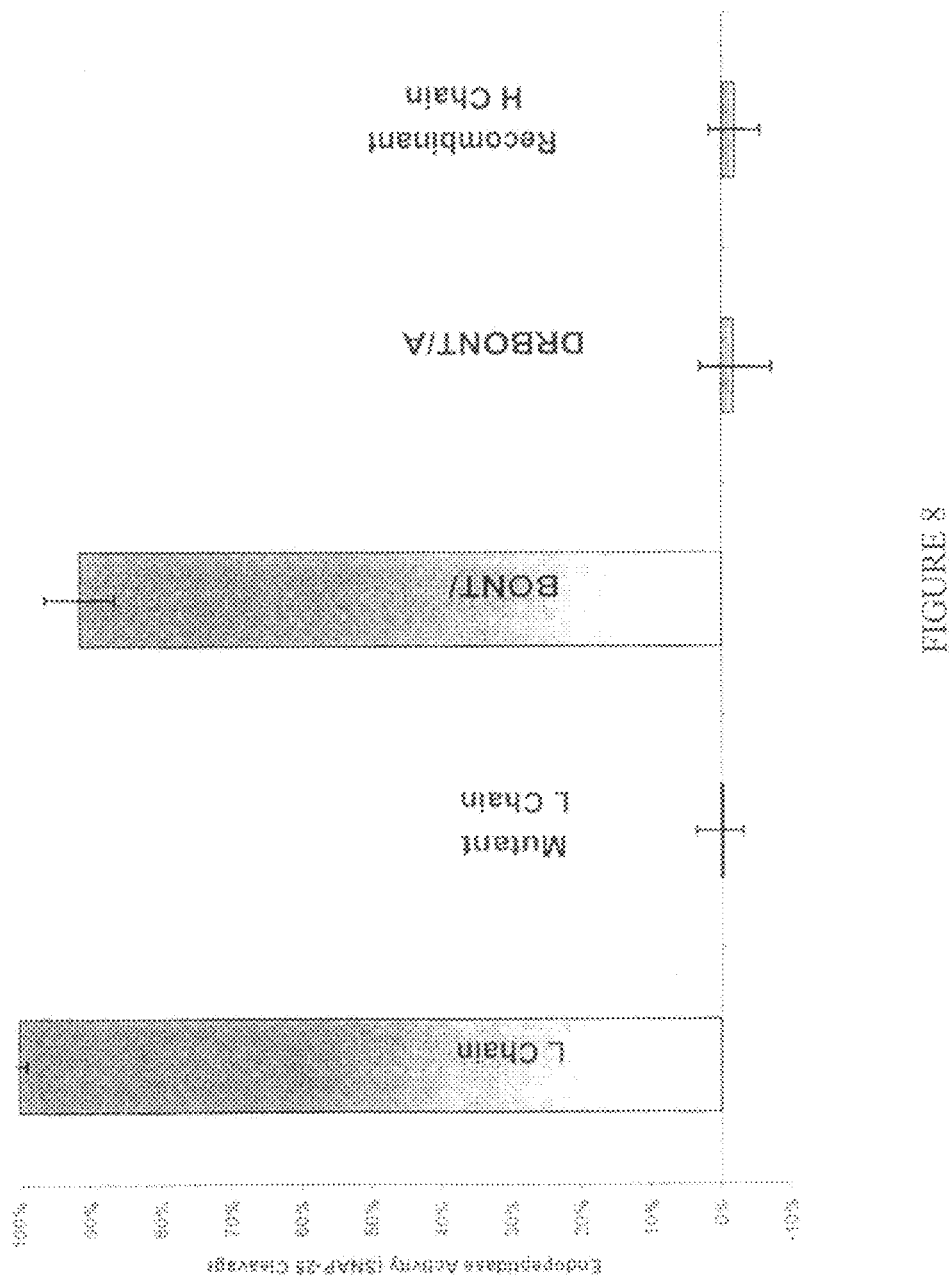

FIG. 8 presents exemplary endopeptidase data showing the activity in the L chain and native BoNT/A protein, but not the double mutant L chain, DR BoNT/A protein, or recombinant H chain.

Figure 9:
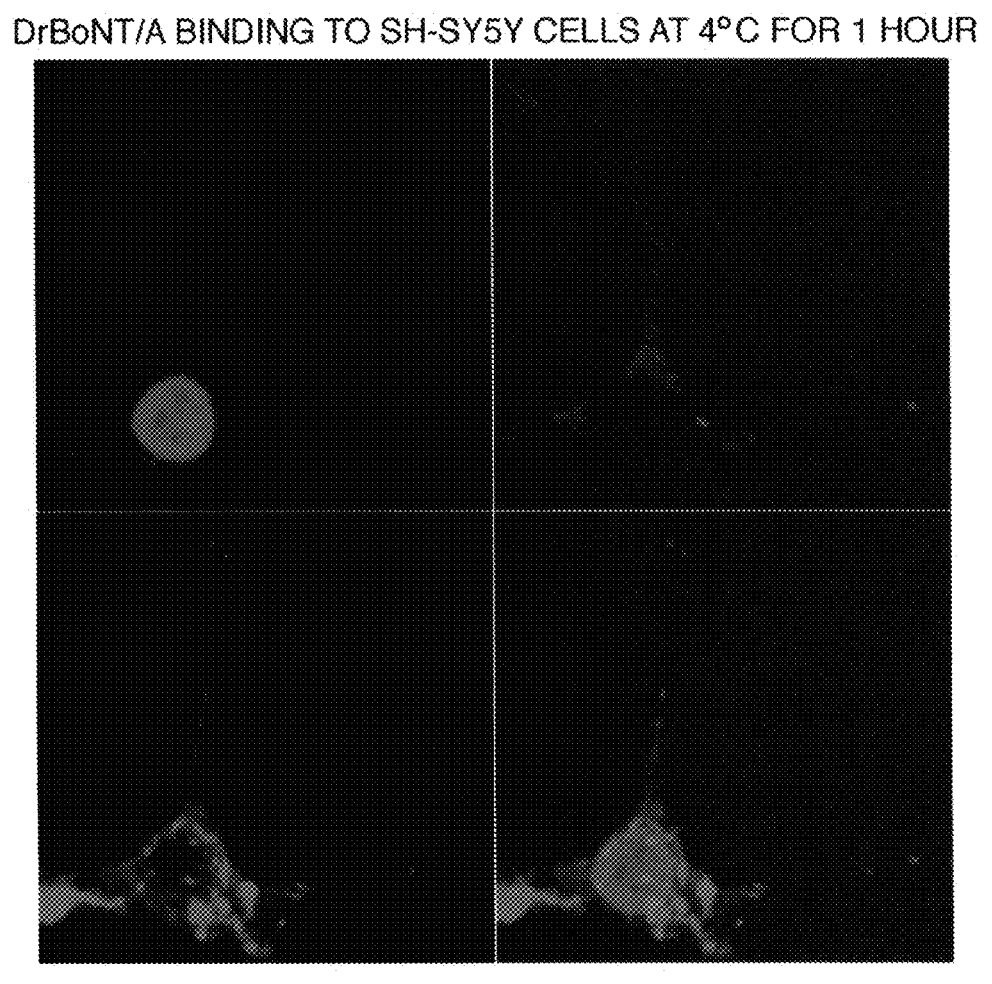

FIG. 9 presents exemplary data showing cell membrane binding of DR BoNT/A.

A: Blue-fluorescent Hoechst 33342 shows nucleus

B: Green-fluorescent FITC shows the binding of DR BoNT/A to SH-SY5Y cells

C: Red-fluorescent Alexa Fluor 594 shows the plasma membrane

D: merged images showing DR BoNT/A bound to the plasma membrane

Figure 10:
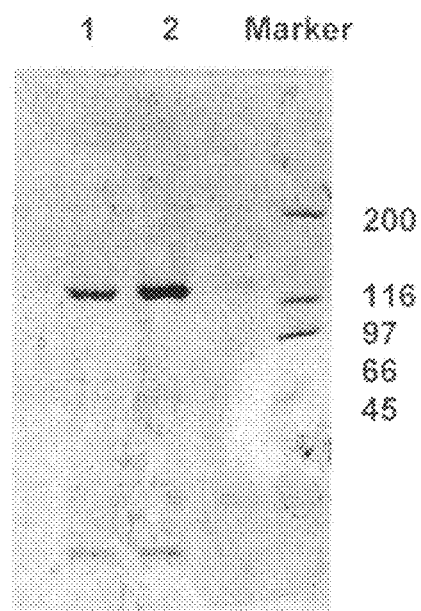

FIG. 10 presents SDS PAGE gel electrophoresis of one embodiment of a triple mutant BoNT/A; H223M/E224A/E262A BoNT/A (DRBoNT/A-T).

Figure 11:
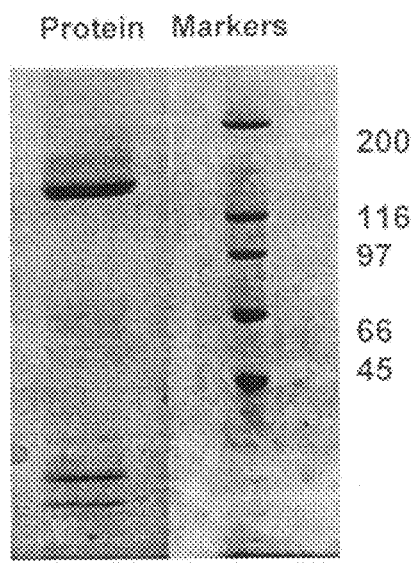

FIG. 11 presents SDS PAGE gel electrophoreses of one embodiment of a quadruple mutant BoNT/A; H223M/E224A/H227Q/E262A BoNT/A (DR BoNT/A-Q)

DETAILED DESCRIPTION OF THE INVENTION

The present invention relates to the isolation, detection, and use of *Clostridium botulinum* neurotoxin derived amino acid and nucleic acid sequences. In one embodiment, the nucleic acids are mutated to create a recombinant detoxified botulinum neurotoxin. In one embodiment, the detoxified neurotoxin is used as a vaccine. In one embodiment, the detoxified neurotoxin is used as a botulinum inhibitor and/or antidote. In one embodiment, the detoxified neurotoxin is used to either detect botulinum intoxication or screen for compounds effective in inhibiting botulinum toxicity.

I. Botulism

*Clostridium botulinum* produces the most poisonous biological toxin known. The lethal human dose is a mere 10-9 mg/kg bodyweight for toxin in the bloodstream. Botulinal toxin blocks nerve transmission to the muscles, resulting in flaccid paralysis. When the toxin reaches airway and respiratory muscles, it results in respiratory failure that can cause death. Amon S., *J. Infect. Dis.* 154:201-206 (1986).

*C. botulinum* spores are carried by dust and are found on vegetables taken from the soil, on fresh fruits, and on agricultural products such as honey. Under conditions favorable to the organism, the spores germinate to vegetative cells which produces toxin. Amon, S., *Ann. Rev. Med.* 31:541 (1980).

Botulism disease may be grouped into four types, based on the method of introduction of toxin into the bloodstream. Food-borne botulism results from ingesting improperly preserved and inadequately heated food that contains botulinal toxin. There were 355 cases of food-borne botulism in the United States between 1976 and 1984. K. L. MacDonald et al., *Am. J. Epidemiol.* 124:794 (1986). The death rate due to botulinal toxin is 12% and can be higher in particular risk groups. C. O. Tacket et al., *Am. J. Med.* 76:794 (1984). Wound-induced botulism results from *C. botulinum* penetrating traumatized tissue and producing toxin that is absorbed into the bloodstream. Since 1950, thirty cases of wound botulism have been reported. M. N. Swartz, "Anaerobic Spore-Forming Bacilli: The Clostridia," pp. 633-646, in B. D. Davis et al., (eds.), Microbiology, 4th edition, J.B. Lippincott Co. (1990). Inhalation botulism results when the toxin is inhaled. Inhalation botulism has been reported as the result of accidental exposure in the laboratory E. Holzer, Med. Klin. 41:1735 (1962) and could arise if the toxin is used as an agent of biological warfare D. R. Franz et al., in Botulinum and Tetanus Neurotoxins, B. R. DasGupta, ed., Plenum Press, New York (1993), pp. 473-476. Infectious infant botulism results from *C. botulinum* colonization of the infant intestine with production of toxin and its absorption into the bloodstream. It is likely that the bacterium gains entry when spores are ingested and subsequently germinate. S. Amon, J. Infect. Dis. 154:201 (1986). There have been 500 cases reported since it was first recognized in 1976. M. N. Swartz, supra.

Infant botulism strikes infants who are three weeks to eleven months old (greater than 90% of the cases are infants less than six months). S. Amon, J. Infect. Dis. 154:201 (1986). It is believed that infants are susceptible, due, in large part, to the absence of the full adult complement of intestinal microflora. The benign microflora present in the adult intestine provide an acidic environment that is not favorable to colonization by *C. botulinum*. Infants begin life with a sterile intestine which is gradually colonized by microflora. Because of the limited microflora present in early infancy, the intestinal environment is not as acidic, allowing for *C. botulinum* spore germination, growth, and toxin production. In this regard, some adults who have undergone antibiotic therapy which alters intestinal microflora become more susceptible to botulism.

An additional factor accounting for infant susceptibility to infectious botulism is the immaturity of the infant immune system. The mature immune system is sensitized to bacterial antigens and produces protective antibodies. Secretory IgA produced in the adult intestine has the ability to agglutinate vegetative cells of *C. botulinum*. S. Amon, J. Infect. Dis. 154:201 (1986). Secretory IgA may also act by preventing intestinal bacteria and their products from crossing the cells of the intestine. S. Amon, Epidemiol. Rev. 3:45 (1981). The infant immune system is not primed to do this.

Clinical symptoms of infant botulism range from mild paralysis, to moderate and severe paralysis requiring hospitalization, to fulminant paralysis, leading to sudden death. S. Amon, Epidemiol. Rev. 3:45 (1981).

The chief therapy for severe infant botulism is ventilatory assistance using a mechanical respirator and concurrent elimination of toxin and bacteria using cathartics, enemas, and gastric lavage. There were 68 hospitalizations in California for infant botulism in a single year with a total cost of over $4 million for treatment. T. L. Fraikovich and S. Amon, West. J. Med. 154:103 (1991).

Different strains of *Clostridium botulinum* each produce antigenically distinct toxin designated by the letters A-G. Serotype A toxin has been implicated in 26% of the cases of food botulism; types B, E and F have also been implicated in a smaller percentage of the food botulism cases. H. Sugiyama, Microbiol. Rev. 44:419 (1980). Wound botulism has been reportedly caused by only types A or B toxins H. Sugiyama, supra. Nearly all cases of infant botulism have been caused by bacteria producing either type A or type B toxin. (Exceptionally, one New Mexico case was caused by *Clostridium botulinum* producing type F toxin and another by *Clostridium botulinum* producing a type B-type F hybrid.) S. Amon, Epidemiol. Rev. 3:45 (1981). Type C toxin affects waterfowl, cattle, horses and mink. Type D toxin affects cattle, and type E toxin affects both humans and birds.

A trivalent antitoxin derived from horse plasma is commercially available from Connaught Industries Ltd. as a therapy for toxin types A, B, and E. However, the antitoxin has several disadvantages. First, extremely large dosages must be injected intravenously and/or intramuscularly. Second, the antitoxin has serious side effects such as acute anaphylaxis which can lead to death, and serum sickness. Finally, the efficacy of the antitoxin is uncertain and the treatment is costly. C. O. Tacket et al., Am. J. Med. 76:794 (1984).

A heptavalent equine botulinal antitoxin which uses only the F(ab')2 portion of the antibody molecule has been tested by the United States Military. M. Balady, USAMRDC Newsletter, p. 6 (1991). This was raised against impure toxoids in those large animals and is not a high titer preparation.

A pentavalent human antitoxin has been collected from immunized human subjects for use as a treatment for infant botulism. The supply of this antitoxin is limited and cannot be expected to meet the needs of all individuals stricken with botulism disease. In addition, collection of human sera must involve screening out HIV and other potentially serious human pathogens. P. J. Schwarz and S. S. Arnon, Western J. Med. 156:197 (1992).

Immunization of subjects with toxin preparations has been done in an attempt to induce immunity against botulinal toxins. A *C. botulinum* vaccine comprising chemically inactivated (i.e., for example, formaldehyde-treated) type A, B,C, D and E toxin is commercially available for human usage. However, this vaccine preparation has several disadvantages. First, the efficacy of this vaccine is variable (in particular, only 78% of recipients produce protective levels of anti-type B antibodies following administration of the primary series). Second, immunization is painful (deep subcutaneous inoculation is required for administration), with adverse reactions being common (moderate to severe local reactions occur in approximately 6% of recipients upon initial injection; this number rises to approximately 11% of individuals who receive booster injections) Informational Brochure for the Pentavalent (ABCDE) *Botulinum* Toxoid, Centers for Disease Control. Third, preparation of the vaccine is dangerous as active toxin must be handled by laboratory workers.

Clearly, current compositions and methods regarding either botulinum antitoxins and/or vaccines are insufficient to provide a safe and effective medical alternative to prevent and/or treat botulism.

II. *Botulinum* Neurotoxins

In one embodiment, the present invention contemplates compositions and methods directed to a non-toxic recombinant botulinum toxin A (DR BoNT/A). In one embodiment, a DR BoNT/A is created by site-specific mutation. Such DR BoNT/A mutants described herein finds applications including, but not limited to: i) research (i.e., for example, into the mechanism of action of BoNT/A, including its binding, translocation, and pharmacokinetics, and for its use to develop and test antidote); ii) antibody development (for therapy and diagnostics); iii) assessing risks and diagnostics for indoor release; iv) for examining pharmacokinetics in mammals, including primates; v) vaccine development; and vi) clinical therapeutic applications.

*Botulinum* neurotoxins (BoNTs) are a group of extremely potent toxins, which are produced by various strains of *Clostridium botulinum*, and in some cases by *C. butirycum* and *C. barati*. Clostridial neurotoxins comprise seven serotypes (A-G) of botulinum neurotoxins (Sollner et al., (1993) Nature 362, 318-324), each produced by *Clostridium botulinum* as a 150 kDa single peptide chain. The protein is post-translationally proteolyzed to form a dichain in which the heavy chain (HC) and light chain (LC) are linked through a disulfide bond (Montecucco and Schiavo, (1995) Q. Rev. Biophys, 28, 423-472). HC is composed of two 50 kDa domains, with the N-terminal half HCN involved in translocation across endosomal membrane and C-terminal half HCC involved in binding to neuronal receptors. LC plays a critical intracellular enzymatic role in the action of BoNT (Montecucco et al., Q. Rev. Biophys, 28, 423-472; Krieglstein et al., J. Protein Chem. 13, 49-57).

A multi-step mechanism is involved in the cell intoxication by BoNTs (Chaddock et al., (2002) Trends Biochem. Sci. 27, 552-558). The neurotoxin binds to the pre-synaptic nerve endings of neurons through a heavy chain (H) and enters by receptor-mediated endocytosis (Schiand, G., Matteoli, M., and Montecucco (2000) Physio. Rev. 80, 717-755). The low pH of endosome is believed to induce channel formation by the HCN, which allows translocation of the LC into the cytosol (Li and Singh (2000) Biochemistry 39, 6466-6474).

Although it is not necessary to understand the mechanism of an invention, it is believed that LC works as a zinc endopeptidase to cleave specifically one of the three different SNARE proteins essential for synaptic vesicle fusion (Montecucco and Schiavo, G (1993) Trends Biochem. Sci. 18, 324-327; Li and Singh, B. R. (1999) Toxin Rev. 18, 95-112). In one embodiment, BoNT/A and/or BoNT/E cleave SNAP-25. In another embodiment, TeNT and/or BoNT/B, /D, /F and /G cleave cellubrevin. In one embodiment, BoNT/C cleaves syntaxin and SNAP-25. Once a SNARE protein is cleaved, the release of a neurotransmitter (i.e., for example, acetylcholine) is prevented, ultimately leading to the flaccid muscle paralysis (Montecucco and Schiavo, "Structure and function of tetanus and botulinum neurotoxins" Q. Rev. Biophys, 28:423-472 (1995).

A botulinum neurotoxin active site is believed to comprise of a HEXXH+E zinc-binding motif (Li et al., (2000) Biochemistry 39, 2399-2405). Type A botulinum neurotoxin crystallography has revealed that H223, H227, and E262 of the HEXXH+E motif directly coordinate the zinc, and E224 coordinates a water molecule as the fourth ligand (Lacy et al., (1998) Nat Struct Biol. 5, 898-902). The general conformation and active site residues appear conserved in all of the clostridial neurotoxins (Agarwal et al., (2005) Biochemistry 44, 8291-8302).

The BoNTs are typical zinc metalloproteases which have unique conserved zinc binding motif (HEXXH+E) in the active site. Although it is not necessary to understand the mechanism of an invention, it is believed that the zinc may be coordinated by two histidines, a glutamate and a water molecule, presumably playing a role in the catalytic activity. For example, the amino acid residues in BoNT/A active site comprise $H^{223}-E^{224}-L^{225}-I^{226}-H^{227}+E^{262}$.

Site-directed mutation studies carried out on BoNT/A and TeNT-LC demonstrate that active site mutations result in either drastically reduced (E224D) or completely abolished (E224Q) endopeptidase activity. (Li et al., (2000) Biochemistry 39, 2399-2405; Binz et al., (2002) Biochemistry 41, 1717-1723; Rigoni et al., Biochemistry and Biophys, Res. Commun 288, 1231-1237; Rossetto et al., (2001) Toxicon 39, 1150-1159). Although it is not necessary to understand the mechanism of an invention, it is believed that this loss of activity is due to an interference with the hydrolysis step and not due to any change in the binding of the SNAP-25 or the $Zn^{2+}$ ligand to the enzyme (Li et al., (2000) Biochemistry 39, 2399-2405). Further, crystal structure and mutagenesis studies have shown that there may be additional distal amino acids residues act as a secondary coordination sites of zinc. Specifically, secondary coordination sites may stabilize zinc binding and substrate specificity (Sharma and Singh 2004 Biochemistry 43, 4791-4798).

A. Characterization of DR BoNT/A

A basic understanding of BoNT's endopeptidase activity and receptor identities is currently known, however, the translocation process is not well understood. Truncated recombinant LC or HC have been utilized mainly due to the poor availability and extreme toxicity of native holo-toxin. Consequently, the present invention contemplates a nontoxic form of the holo-toxin to be utilized for further research and vaccine development. In one embodiment, the non-toxic holo-toxin is created in a recombinant protein expression system.

Experiments conducted during the course of development of embodiments of the present invention resulted in a plasmid harboring the full length BoNT/A gene with two active site E224A/E262A mutation in a His-tagged construction. For example, a full length protein was expressed in *E. coli* as a soluble form, and the biochemical properties were characterized in comparison with the native holo-toxin. The detoxified recombinant BoNT/A (DR BoNT/A) showed no lethality to mice at 100,000 to 1 million mouse $LD_{50}$ dose. DR BoNT/A characterizations for molecular size and amino acid sequence match native BoNT/A. DR BoNT/A, however, lacks endopeptidase activity against SNAP-25.

1. Western Blot Analysis

While both native BoNT/A and DR BoNT/A show very strong reactions with anti-BoNT/A antibody, native BoNT/E shows little or no reactivity. This observation indicates that the anti-BoNT/A antibody utilized herein was specific to BoNT/A. Since Western blot analysis confirms that anti-BoNT/A antibody reacts equally against DR BoNT/A and BoNT/A, one may conclude that these two botulinum proteins expose similar epitopes. See, FIG. 1.

2. Isoelectric Focusing

Native BoNT/A and DR BoNT/A were focused at the same position on an isoelectric (IEF) gel, wherein the pI for native BoNT/A and DR BoNT/A samples was estimated at 6.1-6.3. FIG. 6. This pI range corresponds well with theoretical pI estimates of 6.3 for DR BoNT/A predicted by Expasy® software. This observation indicates that Native BoNT/A and DR BoNT/A not only have similar amino acid compositions, but their secondary and tertiary folding structure is also similar (infra).

3. Endopeptidase Activity

SNAP-25-GST tagged protein has been shown to be a substrate of BoNT/A. Sharma et al., Biochemistry 43:4791-4798 (2004). Reduction of the disulfide bond between the light and heavy chains is required for the endopeptidase activity (Cai et al., (1999) Biochemistry 38, 6903-6910), so 1 mM DTT may be added to the reaction mixture to achieve optimum enzyme activity.

The BoNT/A active site utilizes zinc ($Zn^{2+}$) to perform the endopeptidase catalytic activity. Although it is not necessary to understand the mechanism of an invention, it is believed that the E262 residue directly coordinates the hydrogen bonding of the zinc to relatively nucleophilic water molecules. Li et al., Biochemistry 39:2399-2405 (2000).

Endopeptidase activity of a double mutant BoNT/A L chain, DR BoNT/A protein, and a recombinant BoNT/A H chain was found to be negligible against SNAP-25 as compared to a native BoNT/A and/or a wild-type BoNT/A L chain. FIG. 8. These results show that BoNT/A endopeptidase activity can be removed completely through mutations within the light chain, and that the BoNT/A H chain has no endopeptidase activity on its own. Mutations in either the H and/or L chain can result in abolishing most or all BoNT/A endopeptidase activity. The E224A→E262A mutation removed almost all BoNT/A endopeptidase activity in contrast to native BoNT/A and recombinant LCA wild type endopeptidase activity.

Further, triple and/or quadruple DR BoNT/A mutants are also devoid of endopeptidase activity. (data not shown). Although it is not necessary to understand the mechanism of an invention, it is believed that once the double mutant reforms the catalytic site, further mutation does not reform the active site.

The present invention contemplates a plurality of BoNT/A mutants in relation to the wild type BoNT/A sequence:

| | | |
|---|---|---|
| a) | Wild Type BoNT/A: | $H^{223}$-$E^{224}$-$L^{225}$-$I^{226}$-$H^{227}$ + $E^{262}$ |
| b) | DR BoNT/A: | $H^{223}$-$A^{224}$-$L^{225}$-$I^{226}$-$H^{227}$ + $A^{262}$ |
| c) | DR BoNT/A-T | $M^{223}$-$A^{224}$-$L^{225}$-$I^{226}$-$H^{227}$ + $A^{262}$ |
| d) | DR BoNT/A-Q | $M^{223}$-$A^{224}$-$L^{225}$-$I^{226}$-$Q^{227}$ + $A^{262}$ |

In one embodiment, a double BoNT/A mutant comprises DR BoNT/A. In one embodiment, a triple BoNT/A mutant comprises DR BoNT/A-T. In one embodiment, a quadruple BoNT/A mutant comprises DR BoNT/A-Q.

4. Protein Folding

Quite often recombinant proteins expressed in E. coli do not fold properly into native conformation due to several reasons. For example, the absence of appropriate and compatible chaperones is believed to interfere with proper protein folding. Protein folding may also be affected during extraction and purification procedures. BoNT/A L chain and DR BoNT/A are adequately soluble in aqueous solution such that they are present in the soluble fraction of a bacterial extract. Recombinant H chain (i.e., for example, following E. coli expression), however, forms inclusion bodies that requires harsher treatment for its extraction and purification.

a. Secondary Structure Folding

Figure 3:
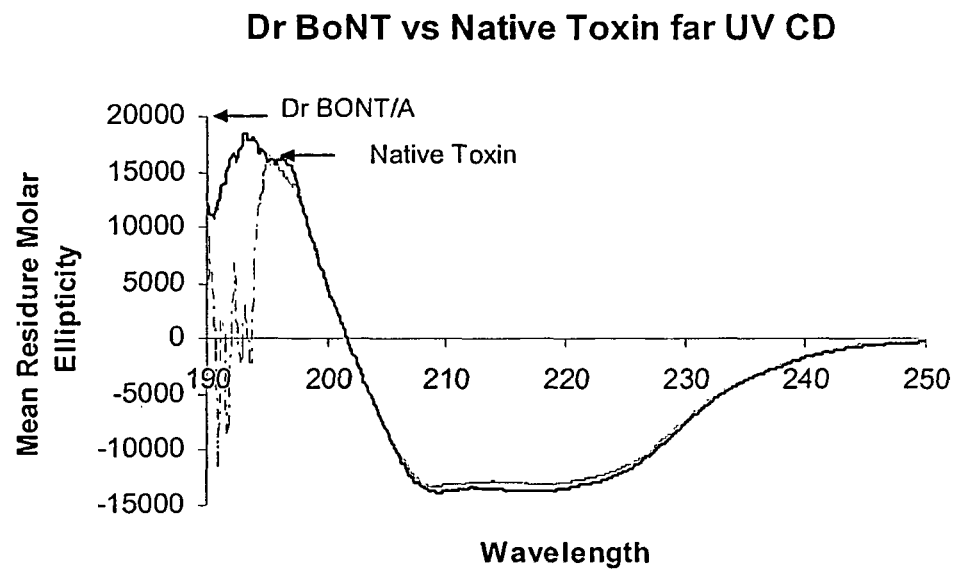

Circular dichroism was employed to compare DR BoNT/A and native BoNT/A protein folding. The CD spectra of DR BoNT/A is virtually identical to native BoNT/A, showing that the secondary structure folding of recombinant DR BoNT/A has not been affected by the mutations. For example, DR BoNT/A and native BoNT/A have two strong absorption maxima at 208 and 222 nm. The signal difference below 200 nm is due to the saturation of the PMT due to the presence of excessive salt. See, FIG. 3. In one embodiment, the present invention contemplates a botulinum vaccine comprising DR BoNT/A, wherein the secondary folding is virtually identical to that of native DR BoNT/A. In one embodiment, the present invention contemplates a DR BoNT/A vaccine comprising an amino acid sequence that is substantially similar to native BoNT/A. In one embodiment, the vaccine amino acid differs from native BoNT/A by two amino acids. Although it is not necessary to understand the mechanism of an invention, it is believed that with only two amino acid residues mutated, and the folding virtually same as the native BoNT/A.

b. Tertiary Structure Folding

In order to assess the tertiary structure folding of DR BoNT/A, its trypsin digestion pattern was compared with that of native BoNT/A. Two different concentrations of trypsin were used to digest DR BoNT/A. The protein concentration for both DR BoNT/A and native BoNT/A was approximately 0.5-0.6 mg/ml. The ratio between protein and trypsin was either 250:1 or 50:1 (w/w). Trypsin digestion was carried out in 50 mM Tris buffer, pH 7.6, containing 200 mM NaCl and 5 mM $CaCl_2$ at room temperature (25° C.) for various periods (5, 10, 30, and 60 min) of incubation. After a given incubation period 20 µl digested mixture was taken out, and 1 mM PMSF was added to it, before boiling it for 5 min with SDS-PAGE loading buffer. Sharma et al., 1998 (supra).

When the trypsin concentration used was low (i.e., for example, at a ratio of protein to enzyme of 250:1), DR BoNT/A was mostly digested into L and H chains. Although it is not necessary to understand the mechanism of an invention, it is believed that DR BoNT is a single peptide, and trypsin nicks it at the same position as in a native BoNT/A (i.e., for example, between amino acid residue 448 and 449).

A comparison of the tertiary folding pattern of DR BoNT/A and native BoNT/A was prepared using a 50:1 (BoNT/A:trypsin, w/w) ratio and digested for a varying periods of time (i.e., for example, 5, 10, 30, and 60 min). Thereafter, the digested samples were boiled in non-reducing and/ or reducing SDS-PAGE-loading buffer for 5 min. A SDS-PAGE analysis showed very similar patterns for native and DR BoNT/A. See, FIG. 4 and FIG. 5, respectively. DR BoNT/A disulfide bonding were formed correctly since the banding patterns were the same as for native BoNT/A under reducing and non-reducing conditions. Additionally, since the proteolytic fragmentation after trypsinization is similar in both DR BoNT/A and native BoNT/A, tertiary structure folding is also expected to be the same, indicating that DR BoNT/A folding corresponds to that of the native BoNT/A.

III. Therapeutic Compositions

A. *Botulinum* Toxin Vaccines

In one embodiment, the present invention contemplates a method comprising administering a non-toxic botulism vaccine. In one embodiment, the vaccine may be administered alone. In one embodiment, the vaccine may be administered in combination with another compound (i.e., for example, another protein such as Hn-33). In one embodiment, the present invention contemplates a botulism vaccine comprising a non-toxic botulinum toxin H chain. In one embodiment, the present invention contemplates a botulism vaccine comprising a non-toxic botulinum toxin L chain. In one embodiment, the present invention contemplates a method of administering a botulism vaccine to a subject. In one embodiment, the administering is selected from the group comprising oral, inhalation, or intraperitoneal injection.

DR BoNT/A provides an ideal candidate for a botulism vaccine because this mutated recombinant protein only differs by two amino acids when compared to the native BoNT/A. Consequently, DR BoNT/A would be expected to retain almost all, or all, antigenic sites present in BoNT/A. In one embodiment, the present invention contemplates a method comprising immunizing mice with a DR BoNT/A to provide immunological protection against a subsequent botulinum toxin challenge.

In one embodiment, the present invention contemplates a method for generating mono- and/or multivalent vaccines for the protection of an animal (i.e., for example, humans) against a plurality of Clostridial species. In one embodiment, the vaccine stimulates the production of a humoral immune response against toxins from *C. botulinum*, *C. tetani*, and *C. difficile*. In one embodiment, the vaccine is created using antigens comprising native and/or recombinantly produced derived Clostridial toxin proteins (i.e., for example, botulinum toxin A). In one embodiment, the recombinantly produced clostridial toxin antigen is detoxified (i.e., for example, detoxified recombinant botulinum toxin A; DR BoNT/A).

Clostridial toxin detoxification may be accomplished by chemical or genetic (i.e., recombinant DNA technology) means. For example, genetic detoxification (i.e., the expression of nontoxic fragments in a host cell) utilizes the expression of nontoxic fragments in a host cell that precludes the presence of intact, active toxin in the final preparation. In contrast, when chemical modification is performed, a toxin is incubated with, for example, formaldehyde.

In one embodiment, the present invention contemplates a botulism vaccine antigen comprising a recombinant *C. botulinum* toxin protein. In one embodiment, the antigen creates a monovalent vaccine preparation. In one embodiment, the antigen creates a multivalent vaccine preparation. Soluble, substantially endotoxin-free recombinant *C. botulinum* type A toxin proteins may be used alone or in conjunction with either recombinant or native toxins or toxoids from *C. botulinum*, *C. difficile* and *C. tetani* as antigens for the preparation of these mono- and multivalent vaccines. It is contemplated that, due to the structural similarity of *C. botulinum* and *C. tetani* toxin proteins, a vaccine comprising *C. difficile* and botulinum toxin proteins (native or recombinant or a mixture thereof) be used to stimulate an immune response against *C. botulinum*, *C. tetani* and *C. difficile*.

The adverse consequences of exposure to botulinal toxin would be avoided by immunization of subjects at risk of exposure to the toxin with nontoxic preparations which confer immunity such as chemically or genetically detoxified toxin.

Vaccines which confer immunity against one or more of the toxin types A, B, E and F would be useful as a means of protecting humans from the deleterious effects of those *C. botulinum* toxins known to affect man. Vaccines which confer immunity against one or more of the toxin types C, D and E would be useful for veterinary applications.

The botulinal neurotoxin may be synthesized as a single polypeptide chain which is processed into a heavy (H) and a light (L) chain; these two chains are held together via disulfide bonds in the active toxin. DasGupta et al., Biochem. Biophys. Res. Commun. 48:108 (1972); DasGupta, *J. Physiol.* 84:220 (1990); Sugiyama, *Microbiol. Rev.* 44:419 (1980). Antisera raised against purified preparations of isolated H and L chains have been shown to protect mice against the lethal effects of the toxin; however, the effectiveness of the two antisera differ with the anti-H sera being more potent (H. Sugiyama, supra).

While the different botulinal toxins show structural similarity to one another, the different serotypes are reported to be immunologically distinct (i.e., for example, sera raised against one toxin type does not cross-react to a significant degree with other types). Thus, the generation of multivalent vaccines may require the use of more than one type of toxin. Purification methods have been reported for native toxin types A, B, C, D, E, and F. Sakaguchi, G., *Pharmac. Ther.* 19:165 (1983). As the different botulinal toxins are structurally related, the invention contemplates the expression of any of the botulinal toxins (e.g., types A-F) as soluble recombinant fusion proteins.

In particular, methods for purification of the type A botulinum neurotoxin have been developed. Moberg et al., *Appl. Environ. Microbiol.* 35:878 (1978). For example, immunization of hens with detoxified purified protein results in the generation of neutralizing antibodies. Thalley et al., In: *Botulinum and Tetanus Neurotoxins*, B. R. DasGupta, ed., Plenum Press, New York (1993), p. 467.

Currently available *C. botulinum* vaccine comprising chemically inactivated (i.e., formaldehyde treated) type A, B, C, D and E toxins is not adequate. The efficacy is variable (in particular, only 78% of recipients produce protective levels of anti-type B antibodies following administration of the primary series) and immunization is painful (deep subcutaneous inoculation is required for administration), with adverse reactions being common (moderate to severe local reactions occur in approximately 6% of recipients upon initial injection; this number rises to approximately 11% of individuals who receive booster injections). Informational Brochure for the Pentavalent (ABCDE) *Botulinum* Toxoid, Centers for Disease Control. Preparation of this vaccine is dangerous as active toxin must be handled by laboratory workers.

In general, chemical detoxification of bacterial toxins using agents such as formaldehyde, glutaraldehyde, or hydrogen peroxide is not optimal for the generation of vaccines or antitoxins. A delicate balance should be struck between too much and too little chemical modification. If the treatment is insufficient, the vaccine may retain residual toxicity. If the treatment is too excessive, the vaccine may lose potency due to destruction of native immunogenic determinants. Another major limitation of using botulinal toxoids for the generation of antitoxins or vaccines is the high production expense. For the above reasons, the development of methods for the production of nontoxic but immunogenic *C. botulinum* toxin proteins is desirable.

*C. botulinum* and *C. tetanus* toxin proteins are believed to have similar structures Schantz et al., *Microbiol. Rev.* 56:80 (1992). The carboxy-terminal 50 kD fragment of the tetanus toxin heavy chain (fragment C) is released by papain cleavage and has been shown to be non-toxic and immunogenic. Recombinant tetanus toxin fragment C has been developed as a candidate vaccine antigen. Makoff et al., *Bio/Technology* 7:1043 (1989). Mice immunized with recombinant tetanus toxin fragment C were protected from challenge with lethal doses of tetanus toxin. No studies have demonstrated that the recombinant tetanus fragment C protein confers immunity against other botulinal toxins such as the *C. botulinum* toxins.

Recombinant tetanus fragment C has been expressed in: i) *E. coli*. Makoff et al., *Nucleic Acids Res.* 17:10191 (1989); and Halpern et al., *Infect. Immun.* 58:1004 (1990); ii) yeast Romanos et al., *Nucleic Acids Res.* 19:1461 (1991); and iii) baculovirus Charles et al., *Infect. Immun.* 59:1627 (1991). Synthetic tetanus toxin genes had been constructed to facilitate expression in yeast and *E. coli* due to the high A-T content of the tetanus toxin gene sequences. Romanos et al., (supra) and Makoff et al., (supra), respectively. High A-T content is a common feature of clostridial genes which creates expression difficulties in *E. coli* and yeast due primarily to altered codon usage frequency and fortuitous polyadenylation sites, respectively. Popoff et al., *Infect. Immun.* 59:3673 (1991); and H. F. LaPenotiere et al., In: *Botulinum and Tetanus Neurotoxins*, B. R. DasGupta, ed., Plenum Press, New York (1993), p. 463.

The C fragment of the *C. botulinum* type A neurotoxin heavy chain has been evaluated as a vaccine candidate. The *C. botulinum* type A neurotoxin gene has been cloned and sequenced Thompson et al., *Eur. J. Biochem.* 189:73 (1990). The C fragment of the type A toxin was expressed as either a fusion protein comprising the botulinal C fragment fused with the maltose binding protein (MBP) or as a native protein. The plasmid construct encoding the native protein was reported to be unstable, while the fusion protein was expressed in inclusion bodies as insoluble protein. Immunization of mice with crudely purified MBP fusion protein resulted in protection against IP challenge with 3 $LD_{50}$ doses of toxin. LaPenotiere et al., (supra). However, this recombinant *C. botulinum* type A toxin C fragment/MBP fusion protein is not a suitable immunogen for the production of vaccines as it is expressed as an insoluble protein in *E. coli*. Furthermore, this recombinant *C. botulinum* type A toxin C fragment/MBP fusion protein was not shown to be substantially free of endotoxin contamination. Experience with recombinant *C. botulinum* type A toxin C fragment/MBP fusion proteins shows that the presence of the MBP on the fusion protein greatly complicates the removal of endotoxin from preparations of the recombinant fusion protein.

Inclusion body protein must be solubilized prior to purification and/or administration to a host. The harsh treatment of inclusion body protein needed to accomplish this solubilization may reduce the immunogenicity of the purified protein. Ideally, recombinant proteins to be used as vaccines are expressed as soluble proteins at high levels (i.e., greater than or equal to about 0.75% of total cellular protein) in *E. coli* or other host cells. This facilitates the production and isolation of sufficient quantities of the immunogen in a highly purified form (i.e., substantially free of endotoxin or other pyrogen contamination). The ability to express recombinant toxin proteins as soluble proteins in *E. coli* is advantageous due to the low cost of growth compared to insect or mammalian tissue culture cells.

The present invention contemplates methods which allow the production of soluble *C. botulinum* toxin proteins in economical host cells (i.e., for example, *E. coli*). Further, methods for the isolation of purified soluble *C. botulinum* toxin proteins which are suitable for immunization of humans and other animals are provided. These soluble, purified preparations of *C. botulinum* toxin proteins provide the basis for improved vaccine preparations and facilitate the production of antitoxin.

When recombinant clostridial toxin proteins produced in gram-negative bacteria (i.e., for example, *E. coli*) are used as vaccines, they are purified to remove endotoxin prior to administration to a host animal. In order to vaccinate a host, an immunogenically-effective amount of purified substantially endotoxin-free recombinant clostridial toxin protein is administered in any of a number of physiologically acceptable carriers known to the art. When administered for the purpose of vaccination, the purified substantially endotoxin-free recombinant clostridial toxin protein may be used alone or in conjunction with known adjuvants, including potassium alum, aluminum phosphate, aluminum hydroxide, Gerbu adjuvant (GmDP; C.C. Biotech Corp.), RIBI adjuvant (MPL; RIBI Immunochemical research, Inc.), QS21 (Cambridge Biotech). The alum and aluminum-based adjuvants are particularly preferred when vaccines are to be administered to humans. The route of immunization may be nasal, oral, intramuscular, intraperitoneal or subcutaneous.

The present invention contemplates using soluble, substantially endotoxin-free preparations of fusion proteins comprising the C fragment of the *C. botulinum* type A toxin as vaccines. In one embodiment, the vaccine comprises the C fragment of the *C. botulinum* type A toxin and a poly-histidine tract (also called a histidine tag). In one embodiment, a fusion protein comprising the histidine tagged C fragment is expressed using the pET series of expression vectors (Novagen). The pET expression system utilizes a vector containing the T7 promoter which encodes the fusion protein and a host cell which can be induced to express the T7 DNA polymerase (i.e., a DE3 host strain). The production of C fragment fusion proteins containing a histidine tract is not limited to the use of a particular expression vector and host strain. Several commercially available expression vectors and host strains can be used to express the C fragment protein sequences as a fusion protein containing a histidine tract (For example, the pQE series (pQE-8, 12, 16, 17, 18, 30, 31, 32, 40, 41, 42, 50, 51, 52, 60 and 70) of expression vectors (Qiagen) which are used with the host strains M15-[pREP4] (Qiagen) and SG13009-[pREP4] (Qiagen) can be used to express fusion proteins containing six histidine residues at the amino-terminus of the fusion protein).

B. *Botulinum* Toxin Inhibitors

In one embodiment, the present invention contemplates a botulinum toxin inhibitor comprising a non-toxic botulinum toxin protein fragment. In one embodiment, the present invention contemplates a botulinum toxin inhibitor comprising a non-toxic botulinum H chain inhibitor. In one embodiment, the H chain inhibitor is derived from DR BoNT/A. Although it is not necessary to understand the mechanism of an invention, it is believed that a non-toxic botulinum toxin fragment binds to neurons in a fashion similar to the native toxin. so it can be used as a inhibitor, since it does not cause botulism at usual dosage.

C. *Botulinum* Light Chain Drug Carriers

In one embodiment, the present invention contemplates a drug delivery system comprising a non-toxin botulinum light (L) chain. In one embodiment, the L chain is attached to a liposome, wherein the liposome comprises a therapeutic drug. In one embodiment, the therapeutic drug is effective against botulism. Although it is not necessary to understand the mechanism of an invention, it is believed that a DR BoNT/A peptide contains an intact light chain component, and thus can be used as a targeted drug delivery system to cells comprising BoNT/A L chain receptors. For example, a drug delivery system comprising DR BoNT/A light chains compete with biologically active (i.e., toxic) light chain in poisoned nerve cells, thereby inhibiting nerve cell damage. Further, an L chain targeted drug delivery system (i.e., a liposome) can provide local administration of therapeutic drugs (i.e., for example, antiinflammatory drugs).

The present invention contemplates several drug delivery systems to which a DR BoNT/A L chain may be attached that provide for roughly uniform distribution, have controllable rates of release and may be administered by a variety of different routes. A variety of different media are described below that are useful in creating drug delivery systems. It is not intended that any one medium or carrier is limiting to the present invention. Note that any medium or carrier may be combined with another medium or carrier; for example, in one embodiment a polymer microparticle carrier attached to a compound may be combined with a liposome medium.

Carriers or mediums contemplated by this invention comprise a material selected from the group comprising gelatin, collagen, cellulose esters, dextran sulfate, pentosan polysulfate, chitin, saccharides, albumin, fibrin sealants, synthetic polyvinyl pyrrolidone, polyethylene oxide, polypropylene oxide, block polymers of polyethylene oxide and polypropylene oxide, polyethylene glycol, acrylates, acrylamides, methacrylates including, but not limited to, 2-hydroxyethyl methacrylate, poly(ortho esters), cyanoacrylates, gelatin-resorcin-aldehyde type bioadhesives, polyacrylic acid and copolymers and block copolymers thereof.

In one embodiment, the present invention contemplates a medical device comprising several components including, but not limited to, a reservoir comprising a carrier comprising a non-toxic BoNT/A L chain, a catheter, a sprayer, and/or a tube. In one embodiment, said medical device administers the carrier either internally or externally to a patient.

One embodiment of the present invention contemplates a drug delivery system comprising at least one pharmaceutical drug effective against a botulinum intoxication and/or secondary conditions thereof. Such pharmaceutical drugs may include, but are not limited to, antiinflammatory, corticosteroid, antithrombotic, antibiotic, antifungal, antiviral, analgesic and anesthetic drugs. In one embodiment, the drug includes, but is not limited to, peptides, proteins, polypeptides and/or fragments thereof. In one embodiment, the drug includes, but is not limited to, nucleic acids, polynucleic acids and/or fragments thereof. In one embodiment, the nucleic acid comprises silencing RNA (siRNA). In one embodiment, the nucleic acid comprises interfering RNA (RNAi). In one embodiment, the polynucleic acid comprises a sense nucleic acid sequence. In one embodiment, the polynucleic acid comprises an antisense nucleic acid sequence.

Microparticles

In one embodiment, the present invention contemplates a medium comprising a microparticle, wherein the microparticle has an attached DR BoNT/A L chain. Preferably, microparticles comprise liposomes, nanoparticles, microspheres, nanospheres, microcapsules, and nanocapsules. Preferably, some microparticles contemplated by the present invention comprise poly(lactide-co-glycolide), aliphatic polyesters including, but not limited to, poly-glycolic acid and poly-lactic acid, hyaluronic acid, modified polysacchrides, chitosan, cellulose, dextran, polyurethanes, polyacrylic acids, psuedo-poly(amino acids), polyhydroxybutrate-related copolymers, polyanhydrides, polymethylmethacrylate, poly (ethylene oxide), lecithin and phospholipids.

Liposomes

In one embodiment, the present invention contemplates liposomes capable of attaching a DR BoNT/A L chain. Liposomes are microscopic spherical lipid bilayers surrounding an aqueous core that are made from amphiphilic molecules such as phospholipids. For example, a liposome may trap various pharmaceutical agents between their hydrophobic tails of the phospholipid micelle. Water soluble drugs can be entrapped in the core and lipid-soluble drugs and/or dissolved in the shell-like bilayer. Liposomes have a special characteristic in that they enable water soluble and water insoluble chemicals to be used together in a medium without the use of surfactants or other emulsifiers. Further, liposomes may form spontaneously by forcefully mixing phospholipids in aqueous media. Water soluble compounds are dissolved in an aqueous solution capable of hydrating phospholipids. Upon formation of the liposomes, therefore, these compounds are trapped within the aqueous liposomal center. The liposome wall, being a phospholipid membrane, holds fat soluble materials such as oils. Liposomes provide controlled release of incorporated compounds (i.e., a pharmaceutical agent). In addition, liposomes can be coated with water soluble polymers, such as polyethylene glycol to increase the pharmacokinetic half-life. One embodiment of the present invention contemplates an ultra high-shear technology to refine liposome production, resulting in stable, unilamellar (single layer) liposomes having specifically designed structural characteristics. These unique properties of liposomes, allow the simultaneous storage of normally immiscible compounds and the capability of their controlled release.

The present invention contemplates cationic and anionic liposomes, as well as liposomes having neutral lipids. Preferably, cationic liposomes comprise negatively-charged materials by mixing the materials and fatty acid liposomal components and allowing them to charge-associate. Clearly, the choice of a cationic or anionic liposome depends upon the desired pH of the final liposome mixture. Examples of cationic liposomes include lipofectin, lipofectamine, and lipofectace.

One embodiment of the present invention contemplates a medium comprising liposomes attached to a DR BoNT/A L chain that provide controlled release of a pharmaceutical agent. Preferably, liposomes that are capable of controlled release: i) are biodegradable and non-toxic; ii) carry both water and oil soluble compounds; iii) solubilize recalcitrant compounds; iv) prevent compound oxidation; v) promote protein stabilization; vi) control hydration; vii) control compound release by variations in bilayer composition such as, but not limited to, fatty acid chain length, fatty acid lipid composition, relative amounts of saturated and unsaturated fatty acids, and physical configuration; viii) have solvent dependency; iv) have pH-dependency and v) have temperature dependency.

Liposome compositions can be broadly categorized into two classifications. Conventional liposomes are generally mixtures of stabilized natural lecithin (PC) that may comprise synthetic identical-chain phospholipids that may or may not contain glycolipids. Special liposomes may comprise: i) bipolar fatty acids; ii) the ability to attach antibodies for tissue-targeted therapies; iii) coated with materials such as, but not limited to lipoprotein and carbohydrate; iv) multiple encapsulation and v) emulsion compatibility.

Liposomes may be easily made in the laboratory by methods such as, but not limited to, sonication and vibration. Alternatively, compound-delivery liposomes are commercially available. For example, Collaborative Laboratories, Inc. are known to manufacture custom designed liposomes for specific delivery requirements.

Microspheres Microparticles and Microcapsules

Microspheres and microcapsules are useful due to their ability to maintain a generally uniform distribution, provide stable controlled compound release and are economical to produce and dispense. Preferably, an associated delivery gel or the compound-impregnated gel is clear or, alternatively, said gel is colored for easy visualization by medical personnel. As used herein, the terms "microspheres, microcapsules and microparticles" (i.e., measured in terms of micrometers) are synonymous with their respective counterparts "nanospheres, nanocapsules and nanoparticles" (i.e., measured in terms of nanometers). Further, the terms "micro/nanosphere, micro/nanocapsule and micro/nanoparticle" are also used interchangeably.

Microspheres are obtainable commercially (Prolease®, Alkerme's: Cambridge, Mass.). For example, a freeze dried DR BoNT/A medium is homogenized in a suitable solvent and sprayed to manufacture microspheres in the range of 20 to 90 μm. Techniques are then followed that maintain sustained release integrity during phases of purification, encapsulation and storage. Scott et al., Improving Protein Therapeutics With Sustained Release Formulations, Nature Biotechnology, Volume 16:153-157 (1998).

Modification of the microsphere composition by the use of biodegradable polymers can provide an ability to control the rate of drug release. Miller et al., Degradation Rates of Oral Resorbable Implants {Polylactates and Polyglycolates: Rate Modification and Changes in PLA/PGA Copolymer Ratios, J. Biomed. Mater. Res., Vol. 11:711-719 (1977).

Alternatively, a sustained or controlled release microsphere preparation is prepared using an in-water drying method, where an organic solvent solution of a biodegradable polymer metal salt is first prepared. Subsequently, a dissolved or dispersed medium of DR BoNT/A is added to the biodegradable polymer metal salt solution. The weight ratio of DR BoNT/A to the biodegradable polymer metal salt may for example be about 1:100000 to about 1:1, preferably about 1:20000 to about 1:500 and more preferably about 1:10000 to about 1:500. Next, the organic solvent solution containing the biodegradable polymer metal salt and DR BoNT/A is poured into an aqueous phase to prepare an oil/water emulsion. The solvent in the oil phase is then evaporated off to provide microspheres. Finally, these microspheres are then recovered, washed and lyophilized. Thereafter, the microspheres may be heated under reduced pressure to remove the residual water and organic solvent.

Other methods useful in producing microspheres that are compatible with a biodegradable polymer metal salt and DR BoNT/A mixture are: i) phase separation during a gradual addition of a coacervating agent; ii) an in-water drying method or phase separation method, where an antiflocculant is added to prevent particle agglomeration and iii) by a spray-drying method.

In one embodiment, the present invention contemplates a medium comprising a microsphere or microcapsule capable of delivering a controlled release of a pharmaceutical agent for a duration of approximately between 1 day and 6 months. Controlled release microcapsules may be produced by using known encapsulation techniques such as centrifugal extrusion, pan coating and air suspension. Microspheres/microcapsules can be engineered to achieve particular release rates. For example, Oliosphere® (Macromed) is a controlled release microsphere system. These particular microsphere's are available in uniform sizes ranging between 5-500 μm and composed of biocompatible and biodegradable polymers. Specific polymer compositions of a microsphere control the drug release rate such that custom-designed microspheres are possible, including effective management of the burst effect. ProMaxx® (Epic Therapeutics, Inc.) is a protein-matrix drug delivery system. The system is aqueous in nature and is adaptable to standard pharmaceutical drug delivery models. In particular, ProMaxx® are bioerodible protein microspheres that deliver both small and macromolecular drugs, and may be customized regarding both microsphere size and desired drug release characteristics.

In one embodiment, a microsphere or microparticle comprises a pH sensitive encapsulation material that is stable at a pH less than the pH of the internal mesentery. The typical range in the internal mesentery is pH 7.6 to pH 7.2. Consequently, the microcapsules should be maintained at a pH of less than 7. However, if pH variability is expected, the pH sensitive material can be selected based on the different pH criteria needed for the dissolution of the microcapsules. The encapsulated compound, therefore, will be selected for the pH environment in which dissolution is desired and stored in a pH preselected to maintain stability. Examples of pH sensitive material useful as encapsulants are Eudragit® L-100 or S-100 (Rohm GMBH), hydroxypropyl methylcellulose phthalate, hydroxypropyl methylcellulose acetate succinate, polyvinyl acetate phthalate, cellulose acetate phthalate, and cellulose acetate trimellitate. In one embodiment, lipids comprise the inner coating of the microcapsules. In these compositions, these lipids may be, but are not limited to, partial esters of fatty acids and hexitiol anhydrides, and edible fats such as triglycerides. Lew C. W., Controlled-Release pH Sensitive Capsule And Adhesive System And Method. U.S. Pat. No. 5,364,634 (herein incorporated by reference).

One embodiment of the present invention contemplates microspheres or microcapsules attached to a DR BoNT/A L chain comprising a pharmaceutical agent. Such pharmaceutical agents include, but are not limited to, antiinflammatory, corticosteriod, antithrombotic, antibiotic, antifungal, antiviral, analgesic and anesthetic.

In one embodiment, a microparticle contemplated by this invention comprises a gelatin, or other polymeric cation having a similar charge density to gelatin (i.e., poly-L-lysine) and is used as a complex to form a primary microparticle. A primary microparticle is produced as a mixture of the following composition: i) Gelatin (60 bloom, type A from porcine skin), ii) chondroitin 4-sulfate (0.005%-0.1%), iii) glutaraldehyde (25%, grade 1), and iv) 1-ethyl-3-(3-dimethylaminopropyl)-carbodiimide hydrochloride (EDC hydrochloride), and ultra-pure sucrose (Sigma Chemical Co., St. Louis, Mo.). The source of gelatin is not thought to be critical; it can be from bovine, porcine, human, or other animal source. Typically, the polymeric cation is between 19,000-30,000 daltons. Chondroitin sulfate is then added to the complex with sodium sulfate, or ethanol as a coacervation agent.

Following the formation of a microparticle, a DR BoNT/A L chain may be directly bound to the surface of the microparticle and/or is indirectly attached using a "bridge" or "spacer". The amino groups of a gelatin lysine group are easily derivatized to provide direct coupling sites. Alternatively, spacers (i.e., linking molecules and derivatizing moieties on targeting ligands) such as avidin-biotin are also useful to indirectly couple targeting ligands to the microparticles. Stability of the microparticle is controlled by the amount of glutaraldehyde-spacer crosslinking induced by the EDC hydrochloride. A controlled release medium is also empirically determined by the final density of glutaraldehyde-spacer crosslinks.

D. *Botulinum* Antidotes

In one embodiment, the present invention contemplates compositions and methods comprising a DR BoNT/A L chain to serve as an antidote against biologically active (i.e., toxic) L chain found in poisoned nerve cells.

In one embodiment, the present invention contemplates a composition comprising a MAb anti-DR BoNT/A L chain antibody. In one embodiment, the antibody reduces the toxicity of a native (i.e., toxic) BoNT/A L chain. Although it is not necessary to understand the mechanism of an invention, it is believed that higher concentrations of the MAb will be found in native BoNT/A intoxicated cells and tissues versus normal cells and tissue. For example, a higher detoxifying affect of monoclonal antibodies has been found in normal cells or tissues versus tumor cells or tissues for anti-digoxin MAbs. Hunter, et al, J. Immunol., 129:1165-1172 (1982).

In one embodiment, anti-DR BoNT/A MAbs may be prepared in hybridomas (i.e., for example, those deposited at ECACC under No. 90011003 on Jan. 12, 1990). EP-A 03416776 and Int. J. Cancer 42:798-802 (1988); and Anticancer Res. 10:129-132 (1990). Briefly, such hybridomas may be obtained by fusing splenocytes of BALB/c mice subjected to an unrelated antigenic stimulus and treated for a short period of time with the specific antigen, as disclosed in U.S. Pat. No. 5,177,016 (herein incorporated by reference). Monoclonal antibodies obtained according to such procedure are able to react with different epitopes of the DR BoNT/A molecule. It is expected that these antibodies possess the property of modulating, at a different degree, the multifactorial type of interaction occurring between native BoNT/A toxins and cell populations. A superior interaction of the anti-DR BoNT/A antibodies is therefore expected, thereby providing a therapeutic (i.e., antidote) effect.

In operative conditions, advantage can be taken from this novel anti-DR BoNT/A MAb property to improve the otherwise narrow therapeutic index of botulism drugs. Indeed, such monoclonal antibodies can be administered to animals, e.g. human patients, affected by botulism intoxication.

In one embodiment, the present invention contemplates a pharmaceutical composition comprising: a) a botulism drug, and b) a monoclonal antibody specific against BoNT/A L chain, wherein said compounds a) and b) may be formulated separately for prior, simultaneous, separate or sequential use in antidotal therapy.

The formulation of the botulism drug can be carried out according to conventional techniques such as lyophilization of an active compound solution in vials, e.g. containing 5, 10 or 20 mg thereof, the 10 mg dosage having been found to be more suitable for use in clinical setting. The MAb preparation for human use should be purified by extended chromatographic procedures based on elution of the active fraction with salt solutions (such as elution buffer: 10 mM citric acid/sodium citrate at pH 5.5 or 3.5 depending on the IgG class). The eluate should eventually be submitted to dialysis through a semipermeable membrane and lyophilized in vials, e.g. containing 25 or 50 mg, of immunoglobulin together with a suitable caking component (such as mannitol).

A plain solution can be obtained by adding sterile water to the lyophilized preparation. Different formulations can be prepared by using, instead of water, balanced salt solutions such as saline buffered solution or Ringer salt solution or similar preparations.

The clinical administration of the anti-BoNT/A MAb is usually by i.v. route, immediately before the injection of a botulism drug, and usually at equal weight ratio therewith. The MAb dosage can be precautionally increased to 1.5-2 weight ratio in high risk patients. The MAb dose can be diminished to 0.5 weight ratio in subjects submitted to short term treatment. The doses of MAb that can be usually reached in clinical practice vary from 50 to 75 mg/square meter of body surface. This dosage is comparable to that commonly used for MAb application in clinical setting.

In the case of extravasation, either of major size or taking place at sites with substantial involvement of vein surround tissues, a MAb solution may be administered by local infiltration. A few general principals, as follows, should be observed for correct application of the MAb. Administration may comprise low amounts of MAb (i.e., for example, at a ¹/₁₀ ratio of a conventional dose), provided that the administration is repeated until the last significant amount of toxin (which is set free by intoxicated cell death) is sequestered by the MAb and detoxified. This procedure is recommended chiefly when the extravasated drug invades loose, areolar or adipose connective tissues. When the extravasation takes place in fibrous, aponeurotic tissue it can happen that a blister is formed, and in this case, an immediate local injection of MAb at high concentrations, (i.e., for example, at a 10× ratio of a conventional dose) should be carried out.

E. *Botulinum* Pharmacokinetic Analysis

In one embodiment, the present invention contemplates a method of determining BoNT/A pharmacokinetics. The ability to accurately determine the distribution, bioavailability and elimination of a toxic substance in a body is hampered by the ethical considerations of administering a harmful compound. Consequently, limited knowledge is available regarding the pharmacokinetic parameters of botulinum toxin.

A deotoxified botulinum toxin that maintains the same physical characteristics (i.e., for example, amino acid sequence and protein folding parameters) as native botulinum toxin would make an ideal candidate for use for pharmacokinetic analysis. In one embodiment, the present invention contemplates a method utilizing DR BoNT/A as a pharmacokinetic marker. Although it is not necessary to understand the mechanism of an invention, it is believed that DR BoNT/A will be distributed and eliminated from a body in an identical fashion as native BoNT/A.

Data describing drug modeling and pharmacokinetics are routinely obtained from standard clinical studies. For example, two comparable, open-label, randomized, parallel, placebo-controlled group comprising healthy volunteers may be utilized. In one group, DR BoNT/A may be administered as eight single SC doses: 300, 450, 600, 900, 1200, 1350, 1800, 2400 IU/kg. In a second group, DR BoNT/A may be administered as multiple dosage regimens: 150 IU/kg three times a week for four weeks and 600 IU/kg one per week for four weeks. Each treatment group may range in size but a minimum of at least 5 subjects is preferred.

Baseline DR BoNT/A concentrations for each subject are determined by averaging the predose values (10, 20 and 30 min). This value is then subtracted from the post-dose values at each time point to obtain the corrected serum DR BoNT/A concentrations. The mean of the corrected concentrations for all subjects is used for data analysis. Any measurement below the limit of assay detection should not be used as a data point.

Intravenous bolus administration can provide preliminary analysis to establish the appropriate compartment analysis.

For example, if a one-compartment model is found to be adequate, the disposition of DR BoNT/A may be nonlinear mainly because of a dose-dependant decrease in clearance. See, Macdougall et al., *Clin. Pharmacokinet.* 20:99-113 (1991). In this case, a Michaelis-Menten function can be used to describe DR BoNT/A disposition. The IV data for DR BoNT/A concentrations ($C_{DR\ BoNT/A}$=Ap/Vd) versus time were fitted with the following equation:

$$\frac{dAp}{dt} = -\left(\frac{V\max}{KmxVd + Ap}\right)Ap$$

where Aρ is the amount of DR BoNT/A in the body, Vmax is the capacity of the process, Km is the affinity constant or the plasma DR BoNT/A concentration at which the elimination rate reaches one-half Vmax, and Vd is the volume of distribution. The IV concentration-time profiles for the various doses of DR BoNT/A would be expected to fit a one-compartment model with non-linear disposition because, as a protein, DR BoNT/A can be expected to be restricted to the intravascular compartment. However, alternative pharmacokinetic compartment model fittings may be performed using commercially available software (i.e., for example, ADAPT II® software (see, e.g., Argenio et al., 1998. ADAPT II User's Guide, Biomedical Simulations Resource, University of Southern California, Los Angeles).

IV. Detection of *Botulinum* Toxin

The invention contemplates detecting a bacterial toxin in a sample. The term "sample" in the present specification and claims is used in its broadest sense. On the one hand it is meant to include a specimen or culture. On the other hand, it is meant to include both biological and environmental samples.

Biological samples may be animal, including human, fluid, solid (i.e., for example, stool) or tissue; liquid and solid food products and ingredients such as dairy items, vegetables, meat and meat by-products, and waste. Environmental samples include environmental material such as surface matter, soil, water and industrial samples, as well as samples obtained from food and dairy processing instruments, apparatus, equipment, disposable and non-disposable items. These examples are not to be construed as limiting the sample types applicable to the present invention.

The invention contemplates detecting bacterial toxin by a competitive immunoassay method that utilizes recombinant toxin A and toxin B proteins, antibodies raised against recombinant bacterial toxin proteins. A fixed amount of the recombinant toxin proteins are immobilized to a solid support (e.g., a microtiter plate) followed by the addition of a biological sample suspected of containing a bacterial toxin. The biological sample is first mixed with affinity-purified or PEG fractionated antibodies directed against the recombinant toxin protein. A reporter reagent is then added which is capable of detecting the presence of antibody bound to the immobilized toxin protein. The reporter substance may comprise an antibody with binding specificity for the antitoxin attached to a molecule which is used to identify the presence of the reporter substance. If toxin is present in the sample, this toxin will compete with the immobilized recombinant toxin protein for binding to the anti-recombinant antibody thereby reducing the signal obtained following the addition of the reporter reagent. A control is employed where the antibody is not mixed with the sample. This gives the highest (or reference) signal.

The invention also contemplates detecting bacterial toxin by a "sandwich" immunoassay method that utilizes antibodies directed against recombinant bacterial toxin proteins. Affinity-purified antibodies directed against recombinant bacterial toxin proteins are immobilized to a solid support (e.g., microtiter plates). Biological samples suspected of containing bacterial toxins are then added followed by a washing step to remove substantially all unbound antitoxin. The biological sample is next exposed to the reporter substance, which binds to antitoxin and is then washed free of substantially all unbound reporter substance. The reporter substance may comprise an antibody with binding specificity for the antitoxin attached to a molecule which is used to identify the presence of the reporter substance. Identification of the reporter substance in the biological tissue indicates the presence of the bacterial toxin.

It is also contemplated that bacterial toxin be detected by pouring liquids (e.g., soups and other fluid foods and feeds including nutritional supplements for humans and other animals) over immobilized antibody which is directed against the bacterial toxin. It is contemplated that the immobilized antibody will be present in or on such supports as cartridges, columns, beads, or any other solid support medium. In one embodiment, following the exposure of the liquid to the immobilized antibody, unbound toxin is substantially removed by washing. The exposure of the liquid is then exposed to a reporter substance which detects the presence of bound toxin. In a preferred embodiment the reporter substance is an enzyme, fluorescent dye, or radioactive compound attached to an antibody which is directed against the toxin (i.e., in a "sandwich" immunoassay). It is also contemplated that the detection system will be developed as necessary (e.g., the addition of enzyme substrate in enzyme systems; observation using fluorescent light for fluorescent dye systems; and quantitation of radioactivity for radioactive systems).

V. *Botulinum* Drug Development Screens

In some embodiments, the present invention provides drug screening assays (e.g., to screen for anti-BoNT/A drugs). The screening methods of the present invention utilize DR BoNT/A proteins identified using the methods of the present invention. For example, in some embodiments, the present invention provides methods of screening for compound that alter (e.g., increase or decrease) the toxicity of BoNT/A proteins. In some embodiments, candidate compounds are antibodies that specifically bind to a BoNT/A protein In one screening method, candidate compounds are evaluated for their ability to alter BoNT/A toxicity by contacting a compound with a cell intoxicated with a BoNT/A protein and then assaying for the effect of the candidate compounds on the intoxicated cell. In some embodiments, the effect of candidate compounds on BoNT/A toxicity is assayed for by detecting the level of cellular apoptosis. Cellular apoptosis can be detected by any suitable method.

Specifically, the present invention provides screening methods for identifying modulators, i.e., candidate or test compounds or agents (e.g., proteins, peptides, peptidomimetics, peptoids, small molecules or other drugs) which bind to BoNT/A products (i.e., for example, toxin proteins and/or receptors thereof) of the present invention, have an inhibitory (or stimulatory) effect on, for example, BoNT/A receptor gene expression. Compounds thus identified can be used to modulate the activity of target gene products either directly or indirectly in a therapeutic protocol, to elaborate the biological function of the target gene product, or to identify compounds that disrupt normal target gene interactions. Compounds which inhibit the binding to, or expression of, BoNT/A receptors are useful in the treatment of BoNT/A intoxication.

In one embodiment, the invention provides assays for screening candidate or test compounds that are substrates of a BoNT/A protein or polypeptide or a biologically active portion thereof. In another embodiment, the invention provides assays for screening candidate or test compounds that bind to or modulate the activity of a BoNT/A protein or polypeptide or a biologically active portion thereof.

The test compounds of the present invention can be obtained using any of the numerous approaches in combinatorial library methods, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678 85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) AntiBoNT/A Drug Des. 12:145).

Numerous examples of methods for the synthesis of molecular libraries have been reported, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412 421 [1992]), or on beads (Lam, Nature 354:82 84 [1991]), chips (Fodor, Nature 364: 555 556 [1993]), bacteria or spores (U.S. Pat. No. 5,223,409; herein incorporated by reference), plasmids (Cull et al., Proc. Nad. Acad. Sci. USA 89:1865 1869 [1992]) or on phage (Scott and Smith, Science 249:386 390 [1990]; Devlin Science 249: 404 406 [1990]; Cwirla et al., Proc. Natl. Acad. Sci. 87:6378 6382 [1990]; Felici, J. Mol. Biol. 222:301 [1991]).

In one embodiment, an assay is a cell-based assay in which a cell that expresses a BoNT/A receptor protein or biologically active portion thereof is contacted with a test compound, and the ability of the test compound to the modulate receptor binding activity is determined. Determining the ability of the test compound to modulate such activity can be accomplished by monitoring, for example, changes in enzymatic activity. The cell, for example, can be of mammalian origin.

The ability of the test compound to modulate a BoNT/A protein binding to a compound, e.g., an antibody, can also be evaluated. This can be accomplished, for example, by coupling the antibody with a radioisotope or enzymatic label such that binding of the antibody can be determined by detected.

Alternatively, the BoNT/A protein is coupled with a radioisotope or enzymatic label to monitor the ability of a test compound to modulate BoNT/A protein binding to a substrate in a complex. For example, compounds (e.g., substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound to interact with a BoNT/A protein with or without the labeling of any of the interactants can be evaluated. For example, a microphysiometer can be used to detect the interaction of a compound with a BoNT/A protein without the labeling of either the compound or the BoNT/A protein (McConnell et al. Science 257:1906 1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and markers.

In yet another embodiment, a cell-free assay is provided in which a BoNT/A protein or biologically active portion thereof is contacted with a test compound and the ability of the test compound to bind to the BoNT/A protein or biologically active portion thereof is evaluated. Preferred biologically active portions of the BoNT/A proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,868,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FRET binding event can be conveniently measured through standard fluorometric detection techniques (i.e., for example, by using a fluorimeter).

In another embodiment, determining the ability of the BoNT/A protein to bind to a target molecule can be accomplished using real-time Biomolecular Interaction Analysis (BIA) (see, e.g., Sjolander and Urbaniczky, Anal. Chem. 63:2338 2345 [1991] and Szabo et al. Curr. Opin. Struct. Biol. 5:699 705 [1995]). "Surface plasmon resonance" or "BIA" detects biospecific interactions in real time, without labeling any of the interactants (e.g., BIAcore™). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either a BoNT/A protein, an anti-BoNT/A antibody, or its target molecule to facilitate separation of complexed from non-complexed forms of one or both of the proteins, as well as to accommodate automation of the assay. Binding of a test compound to a BoNT/A protein, or interaction of a BoNT/A protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-BoNT/A fusion protein or glutathione-S-transferase/target fusion protein can be adsorbed onto glutathione Sepharose beads (Sigma Chemical, St. Louis, Mo.) or glutathione-derivatized microtiter plates, which are then combined with the test compound or the test compound and either the non-adsorbed target protein or BoNT/A protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of BoNT/A markers binding or activity determined using standard techniques. Other techniques for immobilizing either BoNT/A marker proteins or a target molecule on matrices include using conjugation of biotin and streptavidin. Biotinylated BoNT/A marker protein or target molecules can be prepared from biotin-NHS (N-hydroxysuccinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is prelabeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with BoNT/A protein or target molecules but which do not interfere with binding of the BoNT/A protein to its target molecule. Such antibodies can be derivatized to the wells of the plate, and unbound target or BoNT/A protein trapped in the wells by antibody conjugation. Methods for detecting such complexes, in addition to those described above for the GST-immobilized complexes, include immunodetection of complexes using antibodies reactive with the BoNT/A protein or target molecule, as well as enzyme-linked assays which rely on detecting an enzymatic activity associated with the BoNT/A protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284 7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit. 11: 141 8 [1998]; Hageand Tweed J. Chromatogr. Biomed. Sci. Appl 699:499 525 [1997]). Further, fluorescence energy transfer may also be conveniently utilized, as described herein, to detect binding without further purification of the complex from solution.

The assay can include contacting the BoNT/A proteins or biologically active portion thereof with a known compound that binds the BoNT/A protein to form an assay mixture, contacting the assay mixture with a test compound, and determining the ability of the test compound to interact with a BoNT/A protein, wherein determining the ability of the test compound to interact with a BoNT/A protein includes determining the ability of the test compound to preferentially bind to BoNT/A proteins or biologically active portion thereof, or to modulate the activity of a target molecule, as compared to the known compound.

To the extent that BoNT/A proteins can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, BoNT/A proteins can be used as a "bait protein" in a two-hybrid assay or three-hybrid assay (see, e.g., U.S. Pat. No. 5,283,317; Zervos et al., Cell 72:223 232 [1993]; Madura et al., J. Biol. Chem. 268.12046 12054 [1993]; Bartel et al., Biotechniques 14:920 924 [1993]; Iwabuchi et al., Oncogene 8:1693 1696 [1993]; and Brent WO 94/10300; each of which is herein incorporated by reference), to identify other proteins, that bind to or interact with BoNT/A protein ("BoNT/A binding proteins" or "BoNT/A-bp") and are involved in BoNT/A marker activity. Such BoNT/A-bps can be activators or inhibitors of signals by the BoNT/A proteins or targets as, for example, downstream elements of a BoNT/A protein-mediated signaling pathway.

A modulating agent can be identified using a cell-based or a cell free assay, and the ability of the agent to modulate the activity of a BoNT/A protein can be confirmed in vivo, e.g., in an animal such as an animal model for a disease (e.g., an animal with botulism), or a cell line intoxicated with a native BoNT/A protein.

This invention further pertains to novel agents identified by the above-described screening assays. Accordingly, it is within the scope of this invention to further use an agent identified as described herein (e.g., a BoNT/A protein modulating agent, a BoNT/A protein specific antibody, or a BoNT/A protein-binding partner) in an appropriate animal model to determine the efficacy, toxicity, side effects, or mechanism of action, of treatment with such an agent. Furthermore, novel agents identified by the above-described screening assays can be, e.g., used for treatments as described herein.

EXPERIMENTAL

The following examples serve to illustrate certain preferred embodiments and aspects of the present invention and are not to be construed as limiting the scope thereof.

Example I

Designing and Construction of E224A/E262A BoNT/A Plasmid

Genomic DNA of BoNT/A was isolated from C. botulinum Hall strain. The strategy to construct the full length BoNT/A mutant was to fuse BoNT/A-HC into the LC which is already cloned into the pBN3 vector between the EcoRI and PstI sites. The plasmid pBN3 harboring E224A/E262A BoNT/A-LC gene was first constructed based on the E224A single mutant LC constructed previously (Li et al., Biochemistry 39, 2399-2405 2000). A single restriction site of Bsu36I was located at the end of LCA sequence. There is no Bsu36I cutting site in the pBN3 vector, which allowed for the use of Bsu36I and Pst I restriction enzymes to cut the pBN3 vector, containing the LCA gene, producing a sticky end for HCA to be ligated. Using forward primer that matches the base pairs of LCA 3'-end with Bsu36I restriction site and reverse primer which is matched with HCA 3'-terminal with built-in 6×His-tag sequence as well as a PstI restriction enzyme site, PCR was performed using genomic DNA as template to creative a HCA gene with N-terminal overhang end of LCA. The PCR product was separated on a 1% DNA agarose gel and purified with a QIAquick® Gel extraction kit (Qiagen, Valencia, Calif.). The purified PCR product was cut with Bsu36I and PstI restriction enzymes, and then ligated to the previously cut pBN3 vector, containing the E224A/E262A BoNT LC gene.

Example II

Primer Design and PCR Reaction

To create HCA gene with N-terminal overlap with C-terminal of the LCA both forward and reverse primers were designed as follows. The forward primer with Bsu36I site was: 5'-GGCCGCCCCGGGCGATAAAT ATAGTAC-CTAAGGTAAATTACAC-3' (SEQ ID NO: 1), and the reverse primer with 6×His-tag and Pst I site was: 5'-AAAT-TATAATAAACTGCAGG CCTTAGTGATGGTGATGGT-GATGCCCGGGAGTTGGCGGGGCCT-TCAGTGGCCTTT CTCCCCATCCATCATC-3' (SEQ ID NO:2). The PCR reactions were performed in 25 µl total volume containing Accuprimer Pfx Supermix, with 200 µM final concentration of each primer, and 300 ng Clostridium botulinum type A genomic DNA as template. The PCR sample was preheated at 95° C. for 5 min and then 35 cycles of PCR were performed: 95° C. for 15 seconds, 65° C. for 30 seconds and 68° C. for 2 minutes 48 seconds. After the last cycle, the reaction was incubated for an additional 10 min at 68° C. and 4° for storage.

Example III

Cloning HCA Gene into the pBN3 Vector

The PCR product was purified using the gel extraction kit (Qiagen, Valencia, Calif.) to remove the excess primers, enzyme, and template and then double digested with Bsu36I and Pst I (New England Bio-Lab, Beverly, Mass.) restriction enzymes in NEB buffer 3. After double digestion, digested products were separated by running-electrophoresis on a low melting point agarose gel and expected band was cut and purified by gel extraction kit. The products were then ligated overnight at 16° C. to the Bsu36I and Pst I digested and dephosphorylated pBN3 vector containing the LCA gene, by using the T4-ligation kits (Novagen, Damstadt, Germany). The ligated reaction mixture was transformed into the E. coli One shoot Top10 competent cells (Invitrogen, Carlsbad, Calif.), and plated on to a LB-agar plate with 100 µm/ml ampicilin for overnight growth. About 100 colonies were obtained from the plate. Several single colonies were picked up to grow overnight in 5 ml LB media with 100 µm/ml ampicilin. Plasmid (pBN3-WY3) was isolated with S.N.A.P® kit (Invitrogen, Carlsbad, Calif.), and checked with Bsu36I and PstI restriction enzymes. Plasmids with correct DNA size of about 2.8 kb which contain whole HC and partially end of LC were subjected to DNA sequencing. See, FIG. 7.

Example IV

Sequencing of the E224A/E262A BoNT/A Gene in the New Construct

The plasmids with correct enzyme cutting pattern harboring the double mutant BoNT/A gene were sent to Genewiz Inc. (North Brunswick, N.J.) for DNA sequencing. Due to the large size of the BoNT/A gene (ca 4 kb), 8 primers were designed as shown below as part of the sequencing strategy.

```
                                           (SEQ ID NO: 3)
    BoNT/A R518    5'-CATAACCATTTCGCGTAAGATTCA-3'

(SEQ ID NO: 4)
    BoNT/A R1190   5'-TTGACCATTAAAGTTTGCTGCTA-3'

(SEQ ID NO: 5)
    BoNT/A R1809   5'-ACTAATTGTTCTACCCAGCCTAAA-3'

(SEQ ID NO: 6)
    BoNT/A F1649   5'-TGTTCCATTATCTTCGTGCTCA-3'

(SEQ ID NO: 7)
    BoNT/A F2103   5'-AAGAAATGAAAAATGGGATGAGGT-3'

(SEQ ID NO: 8)
    BoNT/A F2417   5'-AACGGTTAGAAGATTTTGATGCT-3'

(SEQ ID NO: 9)
    BoNT/A F2953   5'-TGGACTTTACAGGATACTCAGGAA-3'

(SEQ ID NO: 10)
    BoNT/A F3589   5'-GCATCACAGGCAGGCGTAGA-3'
  (Note: R means reverse primer and F means forward primer)
```

Eight sets of sequencing data for about 800 by each were obtained for the mutant BoNT/A gene in the pBN3 vector from plasmid isolated from a single colony. The data were assembled by a computer program (Software-DNASTAR®) to produce the full length of the double mutant BoNT/A gene. The designed double mutant, his-tag and the full length BoNT/A gene sequence were confirmed by sequencing data.

The new vector harboring the E224A/E262A BoNT/A gene with a his-tag was named pBN3-WY3.

Example V

Expression and Purification of the His-tagged E224A/E262A Double Mutant Recombinant BoNT/A Protein (DR BoNT/A)

The pBN3-WY3 vector was transformed into three different *E. coli* competent cells: One shot Top 10 competent cells (Invitrogen), BL21(DE3) cell and BL21(DE3) Plys competent cells (Novagen) for pilot expression. These three different competent cells containing pBN3-WY3 expression plasmid were separately grown over night on LB-agar plate with 100 ug/ml ampicillin, followed by 5 ml LB media containing 100 μg/ml ampicillin over night culture. Six liter large scale cultures were grown at 37° C. with Lab-Line Incubator shaker Model 3526 (Melrose, Ill.) at the shaking speed 220 rpm until $OD_{600}$ reached to ~0.8, 1 mM IPTG was added to induce DR BoNT/A expression. After induction, cell was grown at 25° C. at reduced shaking speed for overnight. The cell cultures were then harvested at 7000 rpm at 4° C. for 10 min.

The cell pellets were resuspended in lysis buffer (50 mM phosphate buffer, pH 8.0, 300 mM NaCl and protein inhibitor cocktail from Roche (Mannheim, Germany) and 0.5 mg/ml lysozyme (Sigma, St Louis, Mo.). The bacteria suspension was incubated on ice for about 30 min and then sonicated to break the cell membrane. After sonication, the lysate was centrifuged by using Sorvall Instruments centrifuge (Model RC5C, SS34 rotor, Belle Mead, N.J.) at 12,000 rpm for about 45 min to remove the insoluble debris. The supernatant obtained from above was loaded to an already equilibrated Ni-NTA column, and the column was washed with the Buffer (50 mM phosphate pH 8.0, 300 mM NaCl, 1 mM PMSF and 20 mM imidazole). DR BoNT/A protein was eluted from the column at 200 mM imidazole in the above buffer. SDS-PAGE (Sodium dodecyl sulfate-polyacrylamide gel electrophoresis) analysis was carried out to check the purity of each fraction at various imidazole concentrations. Fractions with pure DR BoNT/A protein were pooled together and flash frozen in liquid nitrogen, and stored in a −80° C. freezer.

Example VI

Protein Concentration and pI Determination

Protein concentrations were determined initially by A280 and A320 readings on a UV-vis spectrophotometer (Jasco, Model 550, Boston Mass.) using a Quartz cuvette of 1 cm path length. The formula that was used to calculate the native toxin concentration: (A280-A320)/1.63× dilute factor (1.63 is the extinction coefficient mg/ml at 280 nm of native toxin). An additional quantitative method using Bio-Rad kits (Hercules, Calif.) with BSA as a standard to obtain protein concentration was also used. Similar results were obtained from both methods.

Isoelectric focusing (IEF) was performed to determine the protein isoelectric point pI using the Phast Gel™ System (Pharmacia Biotech, Piscataway, N.J.) under IEF conditions. The Phast Gel™ IEF 3-9 (Amersham Bioscience, Sweden) pH range 3-9 was used, and IEF standards pI 4.45-9.6 from Bio-Rad (Hercules, Calif.) were used as markers. Methods for isoelectric focusing involved three steps: a prefocusing step in which the pH gradient is formed of the gel, a sample application step in which sample and marker were applied on the gel, and focusing step in which protein sample is run on the gel and focused at the same point in the gel matching their pI.

Both DR BoNT and native BoNT/A were loaded on to Phast IEF 3-9 gel after dialyzing off the samples to remove chemicals such as urea and ammonium sulfate. The protein concentration of the two proteins used in IEF experiments was 1 mg/ml. After isoelectric focusing, the gel was fixed in 20% TCA (trichloroacetic acid), washed with destaining solution (30% methanol and 10% acetic acid in double distilled (dd) $H_2O$, and the gel was stained for 1 hour with 0.02% Phast GeP™ Blue solution prepared in about 30% methanol and 10% acetic acid prepared 0.1% (w/v) CuSO4 solution in ddH2O. The gel was then destained in the destaining solution for several hours. The IEF data from the gel was analyzed by Kodak software of Imagine EL Logic100 machine (Eastman Kodak Company, Rochester, N.Y.). The isoelectric point was also calculated by Proteomics tools from Expasy® website based on the amino acid sequence for comparison.

Example VII

Determination of Molecular Weight

The molecular mass of the protein was first calculated using Proteomics tools from Expasy® website based on the amino acid sequence. The molecular weight was also determined with SDS-PAGE using Bio-Rad high molecular weight as standards and Imagine EL Logic100 software.

Example VIII

Endopeptidase Activity

The endopeptidase activity of DR BoNT was estimated by Enzyme-linked Immunosorbant Assay (ELISA) method established previously (Rigoni et al., (2001) Bochemistry and Biophys, Res. Commun 288, 1231-1237). A 96 well microtiter plate was used for the assay. 100 μl of 10 μg/ml SNAP-25-GST fusion protein, which is the BoNT/A substrate, was coated in the plate at 37° C. for about 30 min. 200 nM 100 μl each proteins of LCA, E224A/E262A-LCA, native BoNT/A, DR BoNT/A and HCA were added to the plate. After adding protein samples, 1 mM DTT (dithiothreitol) was added in each well. DTT is known to enhance cleavage activity of BoNT/A (Cai et al., (1999) Biochemistry 38, 6903-6910). The cleavage reactions were allowed to incubate at 37° C. for 90 min. The plate was then washed 2 times with PBS buffer pH 7.4, containing 0.1% Tween-20, and then 1 time with PBS without Tween-20. This was followed by addition of 3% BSA dissolved in PBS buffer 100 μl and incubated for 1 h to block the surface. After washing 3 times with PBS buffer, 85 ng/ml Anti-SNAP-25 IgG from rabbit (Stressgen Biotechnologies Corp, Victoria, Canada) was incubated at 37° C. for 1 hour, After washing 3 times with PBS, a peroxidase-labeled anti-rabbit antibody at 1:10,000 dilution from original 0.8 mg/ml was used as the secondary antibody on the plate; the reaction took place at 37° C. for about 1 hour. A substrate solution containing 0.04% OPD (0-phenylenediamine dihydrochloride) and 0.012% $H_2O_2$ in a 100 mM citrate phosphate buffer, pH 5.0 was used for color development, and the plate was incubated at the room temperature for about 30 min. The reaction was stopped by adding 2 M Sulfuric acid. The color of each well on the plate was measured at 490 nm under a microplate reader (Molecular Devices, Sunnyvale, Calif.).

The SNAP-25 protein alone was used as a control, as were BSA, primary antibody, and secondary antibody to determine control amount of SNAP-25 before cleavage, and to ensure background correction.

Example IX

Circular Dichroism Spectroscopy

Circular Dichroism (CD) data were collected with a JASCO J-715 spectropolarimeter equipped with a computer-controlled temperature cuvette holder. Far UV CD spectra in the region 180-250 nm were recorded with a 1.0 mm path length cell containing 0.1-0.3 mg/ml protein in 25 mM Tris-HCl, pH 8.0, containing 50 mM NaCl. Typically, a scan rate of 20 nm/min, a response time of 8 second, and a bandwidth of 1.0 nm were used. Spectral resolution was 0.5 nm, and 3 scans were averaged for each spectrum. All spectra were corrected for the signal from buffer. All the far UV CD spectra were recorded at room temperature (25° C.). Mean residue weight ellipticities were used to analyze the CD data for comparison of native BoNT/A with Dr BoNT.

Example X

Western Blot Assay

For Western blot analysis, 20 µl of 0.57 mg/ml purified DR BoNT/A and 20 µl of 0.53 mg/ml native BoNT/A were loaded in separate wells of the SDS-PAGE gel. The Kaleidoscope prestained standards were used as markers. SDS-PAGE gel of DR BoNT/A and native BoNT/A were transferred to the PVDF membrane using a Bio-Rad semi-dry TRANS-BLOT® SD Cell (Hercules, Calif.). The transfer process was carried out at 20 watts for 30 min. The transferred membrane was blocked with 3% BSA in PBS buffer, pH 7.4, for 1 h at room temperature, and then incubated with rabbit anti-BoNT/A antibody 0.5 µg/ml (BBTech, Dartmouth, Mass.) for 1 h at room temperature (25° C.). The membrane was then washed 2× with PBST (PBS with 0.1% Tween-20), and 1× with PBS. Anti-rabbit antibody conjugated to alkaline phosphatase from Sigma (Chemical Co., St. Louis, Mo.) at 1:30,000 dilution was added as the secondary antibody, the membrane was incubated at room temperature for another 1 hour, and the membrane was washed similar to the previous washing procedure. 10 µl liquid substrate containing BCIP (5-bromo-4-chloro-3-indolyl-phosphate) and NBT (Nitroblue tetrazolium) Blue (Sigma) was added for the color development. See, FIG. 1.

Example XII

Trypsin Digestion

The protein concentration of both DR BoNT and native BoNT/A was maintained at 0.5-0.6 mg/ml. The ratio between protein and trypsin (Fermentas, Hanover, Md.) was either 250:1 or 50:1 (w/w). Trypsin digestion was carried out in 50 mM Tris buffer, pH 7.6, containing 200 mM NaCl and 5 mM $CaCl_2$ at room temperature (25° C.) for various periods (5, 10, 30, and 60 min) of incubation. After a given incubation period 20 µl digested mixture was taken out, and 1 mM PMSF was added to stop the reaction before boiling it for 5 min with SDS-PAGE loading buffer (Sharma and Singh (1998) Journal of Natural Toxins 7, No 3 239-253). The samples were then analyzed on a 12% SDS-PAGE gel.

Example XIII

Protein Expression, Purification, and Comparison With BoNT/A

The double mutant plasmid DNA with a $His_6$-tag on the C-terminal end was transferred to three different competent cells: Top10, Bl21 (DE3) plys, BL21 (DE3). When the yield of different competent cells was compared, it was found that Bl21 (DE3) gave the best yield of pure protein, ~8 mg/L. During the purification of protein from strain BL21 (DE3), different fractions were loaded on the SDS-PAGE gel to check the purity. Fractions containing pure protein were pooled. A small contamination of smaller proteins (<50 kDa) was found and a Centriprep® YM50 (Millipore, Bedford, Mass.) was used to remove smaller proteins and to concentrate purified protein, or to change buffer. The protein can be stored by adding 20% glycerol in −80° C. Protein precipitate in 0.38 g/ml ammonium sulfate is stable for weeks at 4° C.

The molecular weight of BoNT/A and DR BoNT/A have been determined with SDS-PAGE gel analysis with Bio-Rad high molecular protein marker as standard. For DR BoNT/A the molecular mass was 132 kDa, and that of the native BoNT/A was 133 kDa. See, FIG. 2. Expasy® software for analysis of protein molecular weight and pI revealed that the molecular weight for BoNT/A and DR BoNT were about 150 kDa, and the pI was 6.

Example IVX

Intracellular Delivery of a Drug

This example provides a description of the ability for a drug delivery device as contemplated herein, to provide intracellular delivery of a drug (i.e., for example, a DR BoNT/A related protein, nucleic acid, and/or a small molecule).

A liposome encapsulating DR BoNT/A and/or fragments thereof will be attached to antibodies. The antibodies will have reactivity with a specific diseased tissue (i.e., for example, a cancer tissue). Many cancer specific antigens can be utilized to provide antibodies to allow a targeted delivery of the liposomes. Once the antibodies attach to the cancer specific antigens, the cancer cell engulfs (i.e., for example, by endocytosis) the liposome, wherein the DR BoNT/A related protein, nucleic acid, and/or small molecule is subsequently released into the intracellular space following liposomal dissolution. The released drug will then directly interact with the cancer cell, thereby having a therapeutically beneficial effect.

Example VX

DR BoNT/A Binding to SH-SY5Y Cells

This example provides a cell-based assay demonstrating the binding ability of DR BoNT/A.

Cell Line and Culture Conditions

The human neuroblastoma cell SH-SY5Y was purchased from the American Type Culture Collection (Manassas, Va.). The cells were grown in 1:1 mixture of Eagle's Minimum Essential Medium with non-essential amino acids from ATCC (Manassas, Va.) and Ham's F12 medium from Sigma (St. Louis, Mo.) supplemented with 10% (v/v) fetal bovine serum (ATCC, Manassas, Va.) at 37° C., in a humidified 5% CO2 incubator.

FITC-DRBoNT/A

Recombinant DRBoNT/A was purified in our lab. FITC-labeling of DRBoNT/A was carried out according to the instructions (Sigma).

Treatments of SH-SY5Y Cells with FITC-DRBoNT/A

After seeded the cells in 25 cm2 flask for 48 hours, the cells were rinsed with fresh serum free culture medium once, and treated with 40 nM DRBoNT/A in fresh serum free culture medium for 1 hour at 4° C. The cells were washed with PBS and observed by confocal fluorescence microscopy.

Observations

The results show that DRBoNT/A binds to the neuronal cells at the plasma membrane level. See, FIG. 9.

Example VXI

Preparation of BoNT/A Mutants

Triple mutants H223M/E224A/E262A was created from a full length BoNT/A. Quadruple mutants H223M/E224A/H227Q/E262A was created from DR BoNT/A. Site specific mutations were generated using the commerically available QuikChange® site-direct mutagenesis kit from Stratagene.

MALIH primers:

Forward primer 5' - - - 3'

(SEQ ID NO: 11)
CCG GCA GTA ACT CTG GCA ATG GCC CTC ATC CAC GCT GG

Reverse Primer 5'-3'

(SEQ ID NO: 12)
CCA GCG TGG ATG AGG GCC ATT GCC AGA GTT ACT GCC GG

MALIQ Primers

Forward primer 5' - - - 3'

(SEQ ID NO: 13)
CCG GCA GTA ACT CTG GCA ATG GCC CTC ATC CAA GCT GGTCACCG

Reverse primer 5'-3'

(SEQ ID NO: 14)
CGG TGA CCA GCT TGG ATG AGG GCC ATT GCC AGA GTT AC

The PCR reaction for both mutants includes 5 µl reaction buffer, 2 µl plasmid of DR BoNT (8 mg/ml), 1.25 µl each forward and reverse primer (100 ng/ml each primer), 1 ul enzyme and 39.5 µl H₂O, for a total volume of 50 µl. The PCR condition was 95° C. for 30 seconds for hot start, and 17 cycles of 95° C. 30 seconds, 55° C. for 1 minutes and 68° C. for 7 min 30 seconds. After PCR, the PCR product was digested by using DpnI restriction enzyme and then directly transformed to Top10 competent cell, about 100 colonies growing LB agar plate containing 100 µg/ml AMP. Plasmids have been isolated and send to sequence. The sequence results were confirmed the right mutation.

The two mutant plasmids were transformed to BL21 (DE3) competent cell for protein expression. The purification procedure was followed the exact same method as one of DRBoNT/A. After His-tag column chromatography, pure proteins were obtained for both mutants as analyzed by running SDS-PAGE gel. See, FIG. 10 and FIG. 11, respectively.

Primary characterization has been performed for both mutants and neither show no endopeptidase activity (data not shown).

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

I claim:

1. A composition comprising a non-toxic recombinant type A botulinum protein, wherein said protein comprises a botulinum toxin H (heavy) chain, wherein said protein further comprises a double mutant botulinum toxin L (light) chain, wherein said double mutant comprises E224A/E262A (Glu$^{224}$ to Ala$^{224}$/Glu$^{262}$ to Ala$^{262}$), and wherein said protein further comprises at least one non-botulinum toxin chain selected from the group consisting of a C. difficile toxin and a tetanus toxin.

2. The composition of claim 1, wherein said composition is a vaccine selected from at least one of the group consisting of a botulism vaccine, a tetanus vaccine and a pseudomembranous colitis vaccine.

3. The composition of claim 1, wherein said composition is a botulism antidote.

4. A drug delivery system comprising a composition comprising a non-toxic recombinant type A botulinum protein attached to a carrier wherein said protein comprises a botulinum toxin H (heavy) chain, wherein said protein further comprises a double mutant botulinum toxin L (light) chain, wherein said double mutant comprises E224A/E262A ($Glu^{224}$ to $Ala^{224}$/$Glu^{262}$ to $Ala^{262}$), wherein said protein further comprises at least one non-botulinum toxin selected from the group consisting of a *C. difficile* toxin and a tetanus toxin.

5. The drug delivery system of claim 4, wherein said system further comprises a medical device capable of administering the composition to a diseased tissue.

6. The drug delivery system of claim 4, wherein said carrier comprises a liposome.

7. The drug delivery system of claim 4, wherein said carrier comprises a microparticle.

8. The drug delivery system of claim 5, wherein said medical device is selected from the group consisting of a catheter, a sprayer, and a tube.

9. The drug delivery system of claim 5, wherein said carrier further comprises a drug.

10. The drug delivery system of claim 9, wherein said drug is effective against botulism or secondary considerations thereof.

11. The drug delivery system of claim 9, wherein said drug is selected from the group consisting of antiinflammatory, corticosteroid, antithrombotic, antibiotic, antifungal, antiviral, analgesic and anesthetic drugs.

* * * * *